(12) United States Patent
Klopp

(10) Patent No.: US 11,884,663 B2
(45) Date of Patent: Jan. 30, 2024

(54) SOLID FORMS OF EMETINE

(71) Applicant: Acer Therapeutics, Inc., Newton, MA (US)

(72) Inventor: John Klopp, Martinez, CA (US)

(73) Assignee: Acer Therapeutics, Inc., Newton, MA (US)

(*) Notice: Subject to any disclaimer, the term of this patent is extended or adjusted under 35 U.S.C. 154(b) by 33 days.

(21) Appl. No.: 17/542,165

(22) Filed: Dec. 3, 2021

(65) Prior Publication Data

US 2022/0177469 A1 Jun. 9, 2022

Related U.S. Application Data

(60) Provisional application No. 63/121,743, filed on Dec. 4, 2020.

(51) Int. Cl.
C07D 471/04 (2006.01)

(52) U.S. Cl.
CPC ........ C07D 471/04 (2013.01); *C07B 2200/13* (2013.01)

(58) Field of Classification Search
CPC .................................................. C07D 471/04
USPC ........................................................ 546/112
See application file for complete search history.

(56) References Cited

U.S. PATENT DOCUMENTS

| | | | |
|---|---|---|---|
| 2003/0032203 A1 | 2/2003 | Sabatini et al. | |
| 2014/0105989 A1* | 4/2014 | Anderson | A61K 9/141 424/490 |
| 2021/0236497 A1 | 8/2021 | Smith et al. | |

FOREIGN PATENT DOCUMENTS

WO    WO 2021195521 A1    9/2021

OTHER PUBLICATIONS

"Emetine hydrochloride (Emetini hydrochloridum)," The International Pharmacopoeia, 2016, Sixth Edition.
International Search Report and Witten Opinion, dated Mar. 11, 2022, regarding International Application No. PCT/US2021/061867, 9 pages.
Yin Low et al. "Antiviral Activity of Emetine Dihydrochloride Against Dengue Virus Infection," Journal of Antivirals & Antiretrovirals, 2009, vol. 1, Issue 1, pp. 62-71.

* cited by examiner

*Primary Examiner* — Niloofar Rahmani
(74) *Attorney, Agent, or Firm* — Sheppard Mullin Richter & Hampton LLP

(57) ABSTRACT

Crystalline forms of emetine dihydrochloride (Compound I dihydrochloride) were prepared and characterized in the solid state:

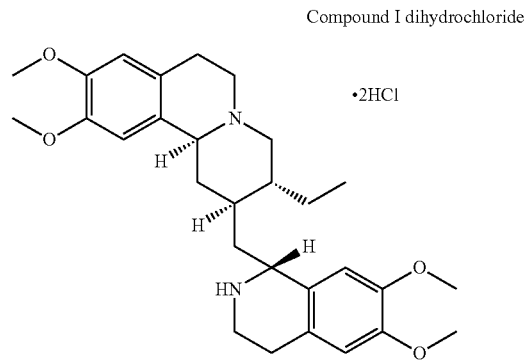

Compound I dihydrochloride

Also provided are processes of manufacture and methods of using the crystalline forms of Compound I dihydrochloride.

27 Claims, 16 Drawing Sheets

SOLID FORMS OF EMETINE

CROSS REFERENCE TO RELATED APPLICATIONS

This application claims the benefit under 35 U.S.C. § 119(e) to U.S. Provisional Application No. 63/121,743, filed Dec. 4, 2020, which is hereby incorporated by reference in its entirety.

FIELD

The present disclosure relates generally to solid forms of emetine, pharmaceutical compositions thereof, therapeutic uses thereof, and processes for making the solid forms.

BACKGROUND

The population continues to be at risk for a variety of viral infections which can be difficult to treat. For example, Zika virus (ZIKV), a mosquito-borne flavivirus, has re-emerged and spread across the Western Hemisphere in the past several years. First isolated in 1947 from a sentinel rhesus macaque in the Zika Forest region of Uganda, ZIKV had remained in relative obscurity for many years until outbreaks in the Pacific islands and then the Americas in the past decade. A large outbreak started in Brazil in late 2014 and is a growing public health concern. About 20% of ZIKV infected individuals develop symptoms, which mostly resemble symptoms caused by other arboviruses, such as dengue viruses or chikungunya virus. Unlike these viruses, however, ZIKV causes congenital defects, including microcephaly, and is also associated with Guillain-Barre syndrome in infected adults.

Since initial reports in December 2019 of an outbreak of severe respiratory illness due to a novel coronavirus (Severe Acute Respiratory Syndrome Coronavirus-2, or SARS-CoV-2) in Wuhan, the disease (COVID-19) has spread rapidly across the globe.

Coronaviruses (CoV) act as cross-species viruses with the potential to rapidly spread into new host species and cause epidemic diseases, as demonstrated by the Middle East respiratory syndrome CoV (MERS-CoV), severe acute respiratory syndrome CoV (SARS-CoV), and the cause of the COVID-19 pandemic, SARS-CoV-2. CoVs represent a group of enveloped, positive-sense, single-stranded viruses with large genomes (27 to 33 kb) and are capable of causing respiratory, enteric, hepatic, and neurological diseases of differing severities.

CoV infections are difficult to prevent and cure. Although CoV replication machinery exhibits substantial proofreading activity, estimates of the nucleotide mutation rate in CoVs are moderate to high relative to that of other single-stranded RNA viruses. Additionally, the large RNA genome in CoVs allows for extra plasticity in genome modification by recombination. Several drugs, such as ribavirin, lopinavir-ritonavir, interferon, and corticosteroids have been used to treat patients infected with SARS-CoV or MERS-CoV. However, contradictory findings on their efficacy and concerns over tolerability and clinical benefit have limited the use of antiviral therapeutics for CoVs.

Therefore, a need exists for effective therapeutic agents for treating diseases caused by viral infections, and that can be obtained in high yields and purity.

SUMMARY

The present disclosure provides solid forms of emetine. Some embodiments provide for a crystalline form of Compound I dihydrochloride:

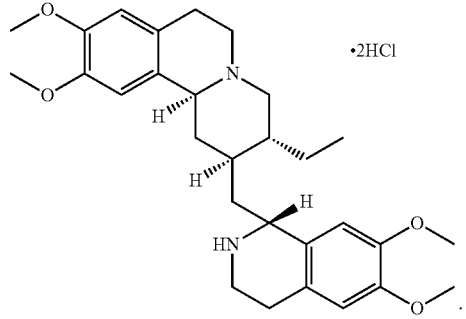

Compound I dihydrochloride

Also described herein are processes for making the forms of Compound I dihydrochloride, pharmaceutical compositions comprising solid forms of Compound I dihydrochloride, and methods for using such forms and pharmaceutical compositions in the treatment of viral infections.

DETAILED DESCRIPTION

Definitions

Figure 1:
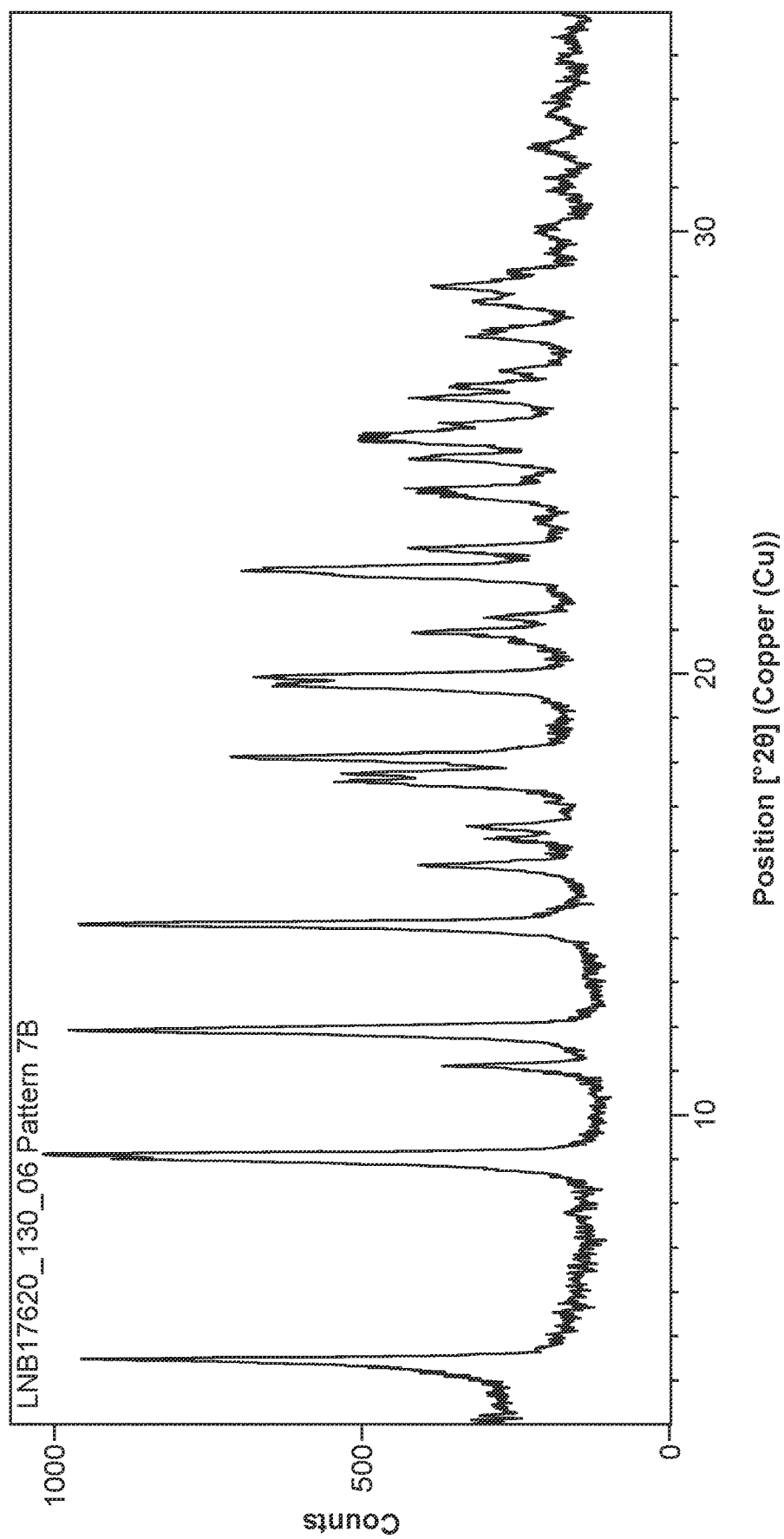
FIG. 1 is an X-ray powder diffractogram of Compound I dihydrochloride Form 7B.

Unless defined otherwise, all technical and scientific terms used herein have the same meaning as is commonly understood by one of ordinary skill in the art. As used herein, the below terms have the following meanings unless specified otherwise. Any methods, devices and materials similar or equivalent to those described herein can be used in the practice of the compositions and methods described herein. The following definitions are provided to facilitate understanding of certain terms used frequently herein and are not meant to limit the scope of the present disclosure. All references referred to herein are incorporated by reference in their entirety.

The term "comprise" and variations thereof, such as, "comprises" and "comprising" are to be construed in an open, inclusive sense, that is, as "including, but not limited to." Further, the singular forms "a," "an," and "the" include plural references unless the context clearly dictates otherwise. Thus, reference to "the compound" includes a plurality of such compounds, and reference to "the assay" includes reference to one or more assays and equivalents thereof known to those skilled in the art.

Reference to "about" a value or parameter herein includes (and describes) embodiments that are directed to that value or parameter per se. In other embodiments, the term "about" includes the indicated amount ±5%. In certain other embodiments, the term "about" includes the indicated amount ±2.5%. In certain other embodiments, the term "about" includes the indicated amount ±1%. Also, to the term "about X" includes description of "X".

Recitation of numeric ranges of values throughout the disclosure is intended to serve as a shorthand notation of referring individually to each separate value falling within the range inclusive of the values defining the range, and each separate value is incorporated in the specification as it were individually recited herein.

Forms of Compound I dihydrochloride are provided herein. In some embodiments, reference to a form of Compound I dihydrochloride means that at least 50% to 99% (e.g., at least 50%, at least 55%, at least 60%, at least 65%, at least 70%, at least 75%, at least 80%, at least 85%, at least 90%, at least 95%, or at least 99%) of Compound I dihydrochloride present in a composition is in the designated form. For instance, in some embodiments, reference to Compound I dihydrochloride Form 7B means that at least 50%, at least 55%, at least 60%, at least 65%, at least 70%, at least 75%, at least 80%, at least 85%, at least 90%, at least 95%, or at least 99% of Compound I dihydrochloride present in a composition is in Form 7B.

The term "solid form" refers to a type of solid-state material that includes amorphous as well as crystalline forms. The term "crystalline form" refers to polymorphs as well as solvates, hydrates, etc. The term "polymorph" refers to a particular crystal structure having particular physical properties such as X-ray diffraction, melting point, and the like.

The term "amorphous" refers to a state in which the material lacks long range order at the molecular level and, depending upon temperature, may exhibit the physical properties of a solid or a liquid. Typically, such materials do not give distinctive X-ray diffraction patterns and, while exhibiting the properties of a solid, are more formally described as a liquid. Upon heating, a change from solid to liquid properties occurs which is characterized by a change of state, typically second order (glass transition).

Any formula or structure given herein, including Compound I dihydrochloride, is also intended to represent unlabeled forms as well as isotopically labeled forms of the compounds. It is understood that for any given atom, the isotopes may be present essentially in ratios according to their natural occurrence, or one or more particular atoms may be enhanced with respect to one or more isotopes using synthetic methods known to one skilled in the art. Thus, hydrogen includes for example $^1$H, $^2$H, $^3$H; carbon includes for example $^{11}$C, $^{12}$C, $^{13}$C, $^{14}$C; oxygen includes for example $^{16}$O, $^{17}$O, $^{18}$O; nitrogen includes for example $^{13}$N, $^{14}$N, $^{15}$N; sulfur includes for example $^{32}$S, $^{33}$S, $^{34}$S, $^{35}$S, $^{36}$S, $^{37}$S, $^{38}$S; fluoro includes for example $^{17}$F, $^{18}$F, $^{19}$F; chloro includes for example $^{35}$Cl, $^{36}$Cl, $^{37}$Cl, $^{38}$Cl, $^{39}$Cl; and the like.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

The term "administering" refers to oral administration, administration as a suppository, topical contact, intravenous, intraperitoneal, intramuscular, intralesional, intranasal or subcutaneous administration, or the implantation of a slow-release device e.g., a mini-osmotic pump, to a subject. Administration is by any route, including parenteral and transmucosal (e.g., buccal, sublingual, palatal, gingival, nasal, vaginal, rectal, ortransdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

In the context of the use, testing, or screening of compounds, the term "contacting" means that the compound(s) are caused to be in sufficient proximity to a particular molecule, complex, cell, tissue, organism, or other specified material that potential binding interactions and/or chemical reaction between the compound and other specified material can occur.

As used herein, the term "subject" or "patient" refers to a living organism that is treated with compounds as described herein, including, but not limited to, any mammal, such as a human, other primates, sports animals, animals of commercial interest such as cattle, farm animals such as horses, or pets such as dogs and cats.

"COVID-19" refers to the coronavirus disease caused by the virus, severe acute respiratory syndrome coronavirus 2 (SARS-CoV-2). COVID-19 was also previously known as the 2019 novel coronavirus.

As used herein, the term "composition" refers to a pharmaceutical preparation suitable for administration to an intended subject for therapeutic purposes that contains at least one pharmaceutically active compound, including any solid form thereof. The composition may include at least one pharmaceutically acceptable component to provide an improved formulation of the compound, such as a suitable carrier or excipient.

In the present context, the term "therapeutically effective" or "effective amount" indicates that the materials or amount of material is effective to prevent, alleviate, or ameliorate one or more symptoms of a disease or medical condition, and/or to prolong the survival of the subject being treated. The therapeutically effective amount will vary depending on the compound, the disorder or condition and its severity and the age, weight, etc., of the mammal to be treated. For example, an effective amount is an amount sufficient to effectuate a beneficial or desired clinical result. The effective amounts can be provided all at once in a single administration or in fractional amounts that provide the effective amount in several administrations. The precise determination of what would be considered an effective amount may be based on factors individual to each subject, including their size, age, injury, and/or disease or injury being treated, and amount of time since the injury occurred or the disease began. One skilled in the art will be able to determine the effective amount for a given subject based on these considerations which are routine in the art.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectables.

The term "pharmaceutically acceptable salt" of a given compound refers to salts that retain the biological effectiveness and properties of the given compound, and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

As used herein, "hydrate" refers to a complex formed by combination of water molecules with molecules or ions of the solute.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

In some embodiments, the phrase "substantially shown in Figure" as applied to an X-ray powder diffractogram is meant to include a variation of ±0.2 °2θ or ±0.1 °2θ, as applied to DSC thermograms is meant to include a variation of ±3° Celsius, and as applied to thermogravimetric analysis (TGA) is meant to include a variation of ±2% in weight loss.

In addition, abbreviations as used herein have respective meanings as follows:

| | |
|---|---|
| ACE2 | angiotensin-converting enzyme 2 |
| ASA | anti-solvent addition |
| CMV | Cytomegalovirus |
| CoV | Coronavirus |
| CRS | Cytokine release syndrome |
| DCM | dichloromethane |
| DMF | dimethylformamide |
| DMSO | dimethylsulfoxide |
| DSC | differential scanning calorimetry |
| DTA | differential thermal analysis |
| DVS | dynamic vapor sorption |
| EBOV | Ebola virus |
| EtOAc | ethyl acetate |
| EtOH | ethanol |
| EV1 | Echovirus 1 |
| h | hour |
| HIV-1 | Human immunodeficiency virus 1 |
| HMPV | Human metapneumorivus |
| HPLC | high performance liquid chromatography |
| HSV-2 | herpes simplex virus type 2 |
| ICU | intensive care unit |
| IPAc | isopropyl acetate |
| kb | kilobase |
| Me | methyl |
| MEK | methyl ethyl ketone |
| MeOH | methanol |
| MERS | Middle East respiratory syndrome |
| MiBK | methyl isobutyl ketone |
| min | minute |
| MTBE | methyl tert-butyl ether |
| NMP | N-methyl pyrrolidone |
| PTFE | Polytetrafluoroethylene |
| RABV | Rabies lyssavirus |
| RH | relative humidity |
| RT | room temperature |
| RVFV | Rift Valley fever virus |
| s | second |
| tBME | t-butyl methyl ether |
| TGA | thermogravimetric analysis |
| THF | tetrahydrofuran |
| v/v | volume to volume |
| wt % | weight percent |
| w/w | weight to weight |
| XRPD | X-ray powder diffraction |
| ZIKV | Zika virus |

Compound I and Compositions Thereof

Emetine, also known as (2S,3R,11bS)-2-(((R)-6,7-dimethoxy-1,2,3,4-tetrahydroisoquinolin-1-yl)methyl)-3-ethyl-9, 10-dimethoxy-1,3,4,6,7,11b-hexahydro-2H-pyrido[2,1-a]isoquinoline (referred herein as "Compound I" or "Compound I free base"), has the following structure:

Compound I

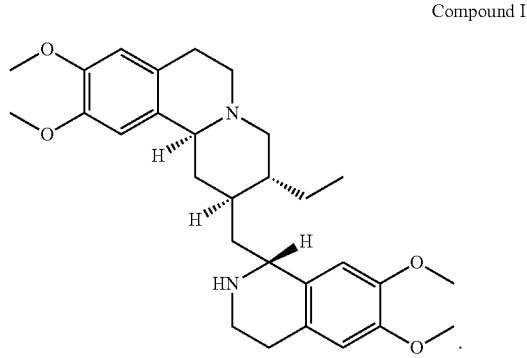

Compound I is used mainly as an antiprotozoal and an emetic. Compound I can also be used in the treatment of viral infections.

The synthesis of Compound I is known in the art. Compound I, or pharmaceutically acceptable salts thereof, also are commercially available.

Provided herein are various solid forms of Compound I. In some embodiments, the present disclosure provides for crystalline forms of Compound I dihydrochloride and processes for making such crystalline forms. It is contemplated that the crystalline forms provided herein can be isolated in high yields and purity.

In some embodiments, Compound I is a free base. In some embodiments, Compound I is a hydrate. In some embodiments, Compound I is a salt. In some embodiments, Compound I is a pharmaceutically acceptable salt. In some embodiments, Compound I is an amorphous form.

Some embodiments provide for a crystalline form of Compound I dihydrochloride selected from: Compound I dihydrochloride Form 7B, Compound I dihydrochloride Form 2, Compound I dihydrochloride Form 3, Compound I dihydrochloride Form 4, Compound I dihydrochloride Form 5, Compound I dihydrochloride Form 6, Compound I dihydrochloride Form 7A, and Compound I dihydrochloride Form 8.

Compound I dihydrochloride Form 7B

The present disclosure provides, in some embodiments, a crystalline form (2S,3R,11bS)-2-(((R)-6,7-dimethoxy-1,2,3,4-tetrahydroisoquinolin-1-yl)methyl)-3-ethyl-9,10-dimethoxy-1,3,4,6,7,11b-hexahydro-2H-pyrido[2,1-a]isoquinoline dihydrochloride ("Compound I dihydrochloride Form 7B" or "Form 7B") characterized by an X-ray powder diffractogram comprising the following peaks: 4.5, 9.1, 11.9, and 14.4 °2θ±0.2 °2θ, as determined on a diffractometer using Cu-Kα radiation. In some embodiments, the diffractogram of Compound I dihydrochloride Form 7B further comprises one or more peaks at: 18.1, 20.0, or 22.3 °2θ±0.2 °2θ. In some embodiments, Compound I dihydrochloride Form 7B is characterized by the X-ray powder diffractogram as substantially shown in FIG. 1.

Figure 2:
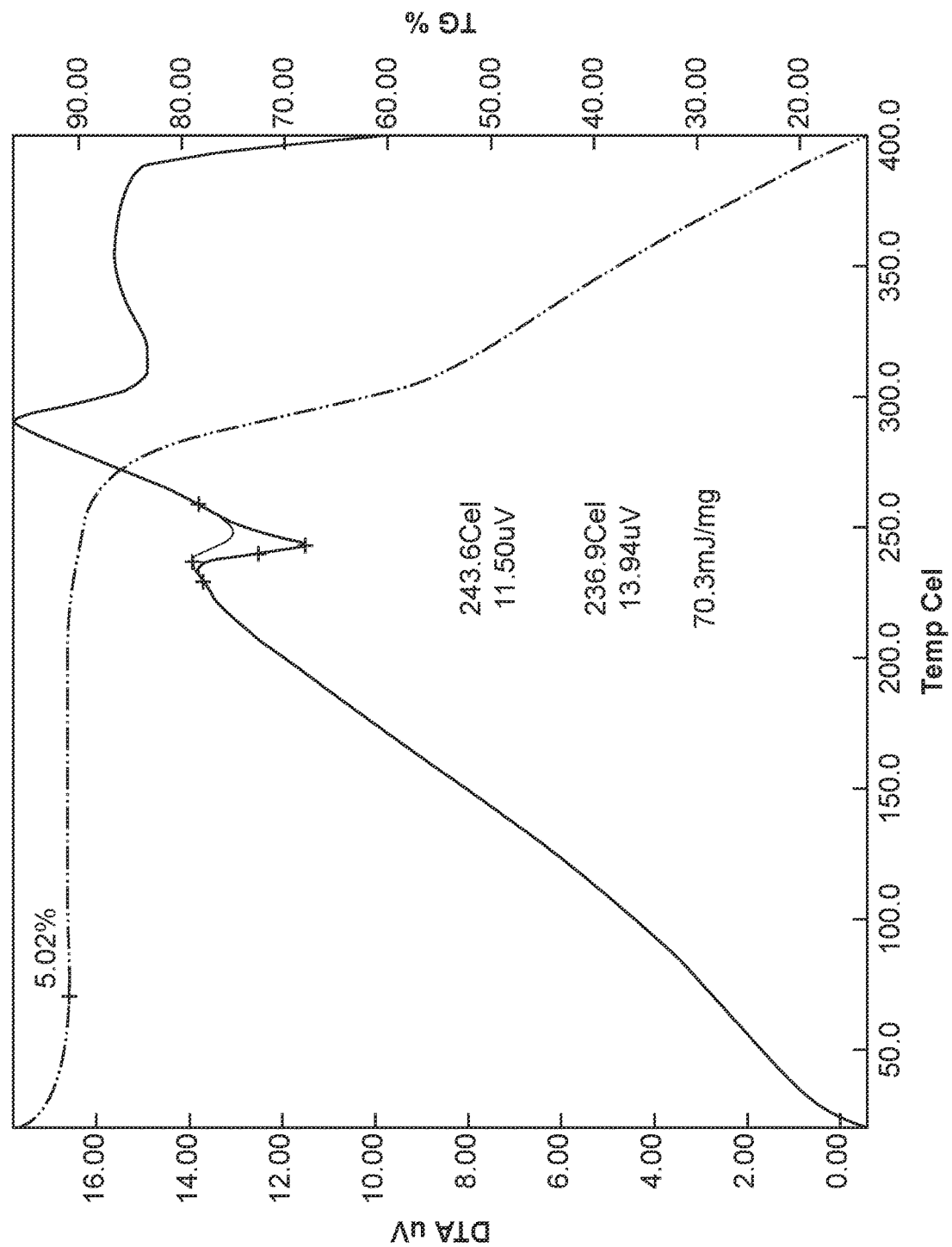
FIG. 2 is a thermogravimetric analysis (TGA) (top line) and a differential thermal analysis (DTA) (bottom line) curve of Compound I dihydrochloride Form 7B.

In some embodiments, Compound I dihydrochloride Form 7B is characterized by a differential thermal analysis (DTA) curve that comprises an endotherm at about 242° C. (onset temperature). In some embodiments, Compound I dihydrochloride Form 7B is characterized by the DTA curve as substantially shown in FIG. 2 (bottom line).

In some embodiments, Compound I dihydrochloride Form 7B is characterized by a thermogravimetric analysis (TGA) thermogram showing weight loss of about 5.0% from the outset to about 75° C. In some embodiments, Compound I dihydrochloride Form 7B is characterized by the thermogram as substantially shown in FIG. 2 (top line).

Some embodiments provide for a method of preparing Compound I dihydrochloride Form 7B comprising:
 a. dissolving Compound I dihydrochloride at about 55° C. to at 65° C. in ethanol:water 99:1 v/v to form a first solution;
 b. filtering the first solution;
 c. cooling the first solution to about 45° C. to about 55° C.;
 d. charging 0.5 volumes of heptane to the first solution to provide a second solution comprising a heptane content of about 5% v/v;
 e. seeding the second solution with Compound I dihydrochloride Form 7B to form a first mixture;
 f. stirring the first mixture at about 45° C. to about 55° C.;
 g. charging 12.5 volumes of heptane to the first mixture to provide a second mixture comprising a heptane content of about 60% v/v;
 h. cooling and stirring the second mixture at about 2° C. to about 8° C.;
 i. filtering the second mixture to isolate solids; and
 j. drying the solids at about 30° C. to about 40° C. under vacuum to provide Compound I dihydrochloride Form 7B.

In some embodiments, step (a) comprises a temperature of about 60° C. In some embodiments, step (b) comprises polish filtering the first solution. In some embodiments, step (b) comprises a temperature of about 60° C. In some embodiments, step (c) comprises a temperature of about 50° C. In some embodiments, step (e) comprises seeding the second solution with 1 wt. % of Compound I dihydrochloride Form 7B. In some embodiments, step (f) comprises a temperature of about 50° C. In some embodiments, step (h) comprises a temperature of about 5° C. In some embodiments, step (h) comprises cooling the second mixture to about 5° C. and subsequently stirring the second mixture at about 5° C. for at least 3 hours.

Compound I dihydrochloride Form 1

Figure 3:
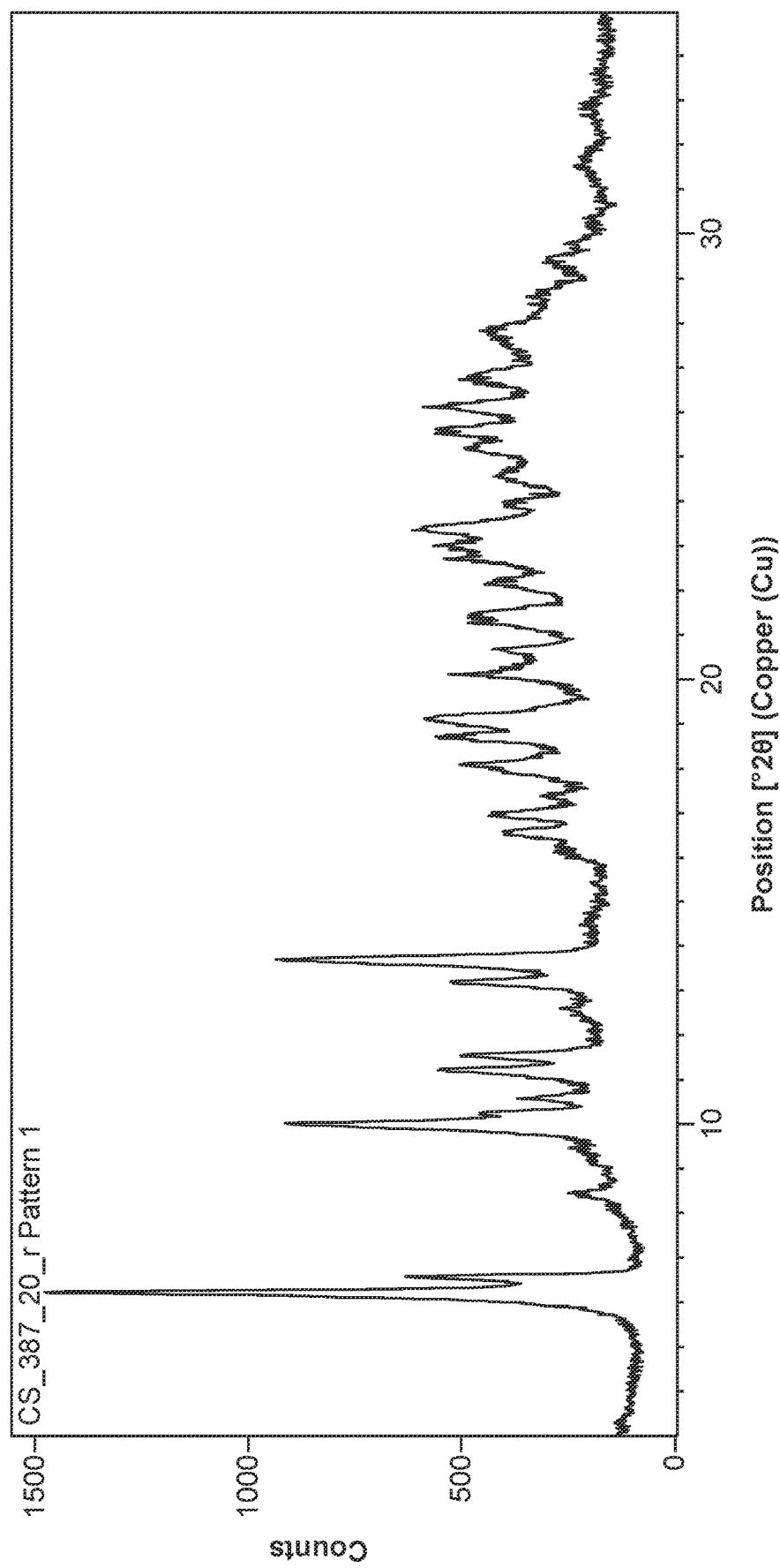
FIG. 3 is an X-ray powder diffractogram of Compound I dihydrochloride Form 1.

The present disclosure provides, in some embodiments, a crystalline form (2S,3R,11bS)-2-(((R)-6,7-dimethoxy-1,2,3,4-tetrahydroisoquinolin-1-yl)methyl)-3-ethyl-9,10-dimethoxy-1,3,4,6,7,11b-hexahydro-2H-pyrido[2,1-a]isoquinoline dihydrochloride ("Compound I dihydrochloride Form 1" or "Form 1"), wherein Compound I dihydrochloride Form 1 is characterized by an X-ray powder diffractogram comprising the following peaks: 6.2, 10.0, 13.7, and 23.3 °2θ±0.2 °2θ, as determined on a diffractometer using Cu-Kα radiation. In some embodiments, the diffractogram of Compound I dihydrochloride Form 1 further comprises one or more peaks at: 11.2, 18.7, or 26.1 °2θ±0.2 °2θ. In some embodiments, Compound I dihydrochloride Form 1 is characterized by the X-ray powder diffractogram as substantially shown in FIG. 3.

Figure 4:
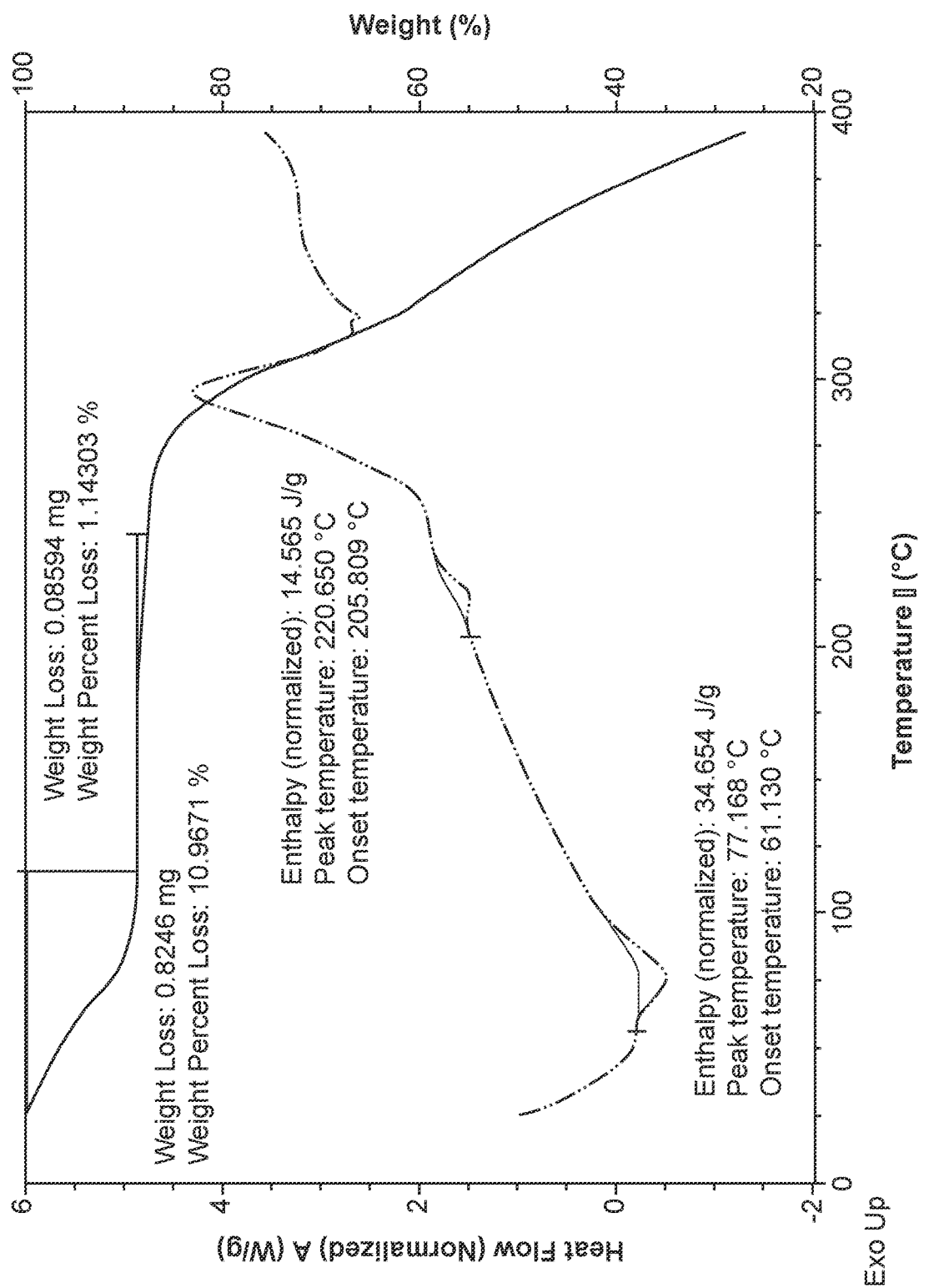
FIG. 4 is a thermogravimetric analysis (TGA) (top line) and a differential scanning calorimeter (DSC) (bottom line) curve of Compound I dihydrochloride Form 1.

In some embodiments, Compound I dihydrochloride Form 1 is characterized by a differential scanning calorimetry (DSC) curve that comprises an endotherm at about 61° C. (onset temperature). In some embodiments, the DSC curve of Compound I dihydrochloride Form 1 comprises an additional endotherm at about 206° C. (onset temperature). In some embodiments, Compound I dihydrochloride Form 1 is characterized by the DSC curve as substantially shown in FIG. 4 (bottom line).

In some embodiments, Compound I dihydrochloride Form 1 is characterized by a thermogravimetric analysis (TGA) thermogram showing a weight loss of about 11.0% from the outset up to 115° C., followed by loss of about 1.1% between 115-240° C. In some embodiments, Compound I dihydrochloride Form 1 is characterized by the thermogram as substantially shown in FIG. 4 (top line).

Compound I dihydrochloride Form 2

The present disclosure provides, in some embodiments, a crystalline form (2S,3R,11bS)-2-(((R)-6,7-dimethoxy-1,2,3,4-tetrahydroisoquinolin-1-yl)methyl)-3-ethyl-9,10-dimethoxy-1,3,4,6,7,11b-hexahydro-2H-pyrido[2,1-a]isoquinoline dihydrochloride ("Compound I dihydrochloride Form 2" or "Form 2") characterized by an X-ray powder diffractogram comprising the following peaks: 6.4, 10.2, 13.6, and 17.0 °2θ±0.2 °2θ, as determined on a diffractometer using Cu-Kα radiation. In some embodiments, the diffractogram of Compound I dihydrochloride Form 2 further comprises one or more peaks at: 20.4 or 25.1 °2θ±0.2 °2θ. In some embodiments, Compound I dihydrochloride Form 2 is characterized by the X-ray powder diffractogram as substantially shown in FIG. 5.

Figure 6:
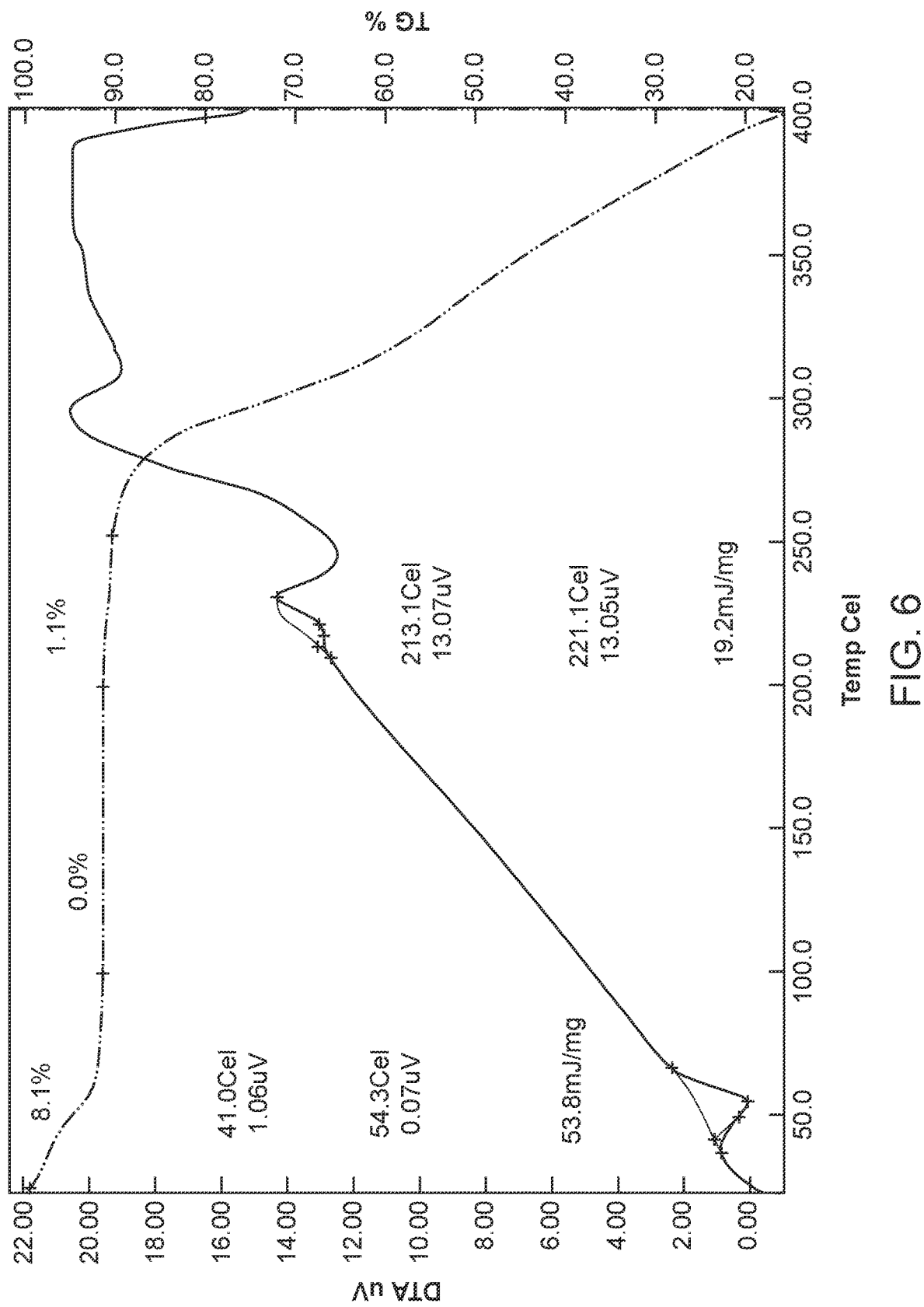
FIG. 6 is a thermogravimetric analysis (TGA) (top line) and a differential thermal analysis (DTA) (bottom line) curve of Compound I dihydrochloride Form 2.

In some embodiments, Compound I dihydrochloride Form 2 is characterized by a differential thermal analysis (DTA) curve that comprises an endotherm at about 41° C. (onset temperature). In some embodiments, the DTA curve of Compound I dihydrochloride Form 2 comprises an additional endotherm at about 213° C. (onset temperature). In some embodiments, Compound I dihydrochloride Form 2 is characterized by the DTA curve as substantially shown in FIG. 6 (bottom line).

In some embodiments, Compound I dihydrochloride Form 2 is characterized by a thermogravimetric analysis (TGA) thermogram showing a weight loss of about 8.10% from the outset to 100° C., followed by weight loss of 1.1% between 200-250° C. In some embodiments, Compound I dihydrochloride Form 2 is characterized by the thermogram as substantially shown in FIG. 6 (top line).

Compound I dihydrochloride Form 3

Figure 7:
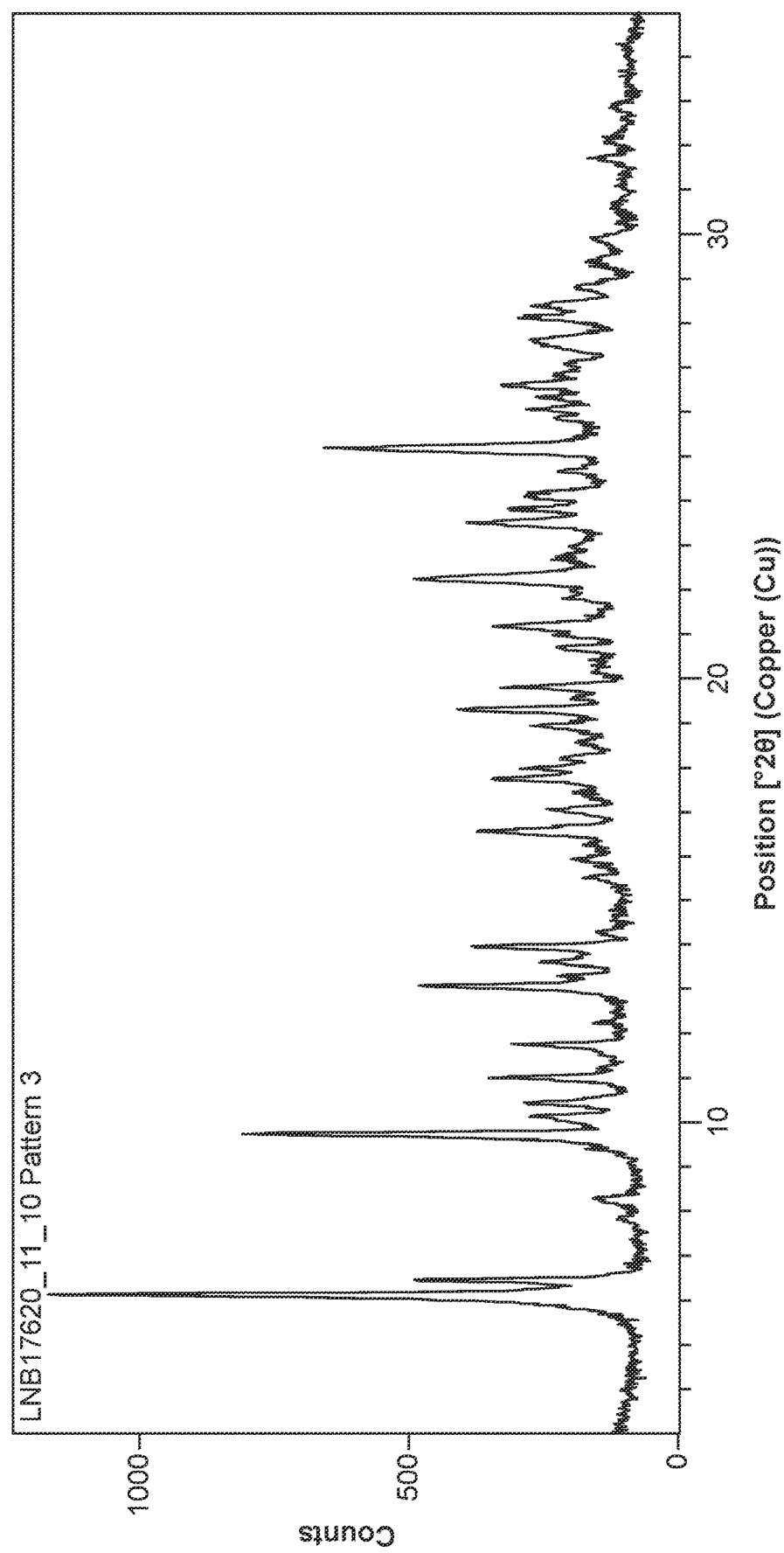
FIG. 7 is an X-ray powder diffractogram of Compound I dihydrochloride Form 3.

The present disclosure provides, in some embodiments, a crystalline form (2S,3R,11bS)-2-(((R)-6,7-dimethoxy-1,2,3,4-tetrahydroisoquinolin-1-yl)methyl)-3-ethyl-9,10-dimethoxy-1,3,4,6,7,11b-hexahydro-2H-pyrido[2,1-a]isoquinoline dihydrochloride ("Compound I dihydrochloride Form 3" or "Form 3") characterized by an X-ray powder diffractogram comprising the following peaks: 6.1, 9.8, and 25.2 °2θ±0.2 °2θ, as determined on a diffractometer using Cu-Kα radiation. In some embodiments, the diffractogram of Compound I dihydrochloride Form 3 further comprises one or more peaks at: 6.5, 13.1, and 22.2 °2θ±0.2 °2θ. In some embodiments, Compound I dihydrochloride Form 3 is characterized by the X-ray powder diffractogram as substantially shown in FIG. 7.

Compound I dihydrochloride Form 4

Figure 8:
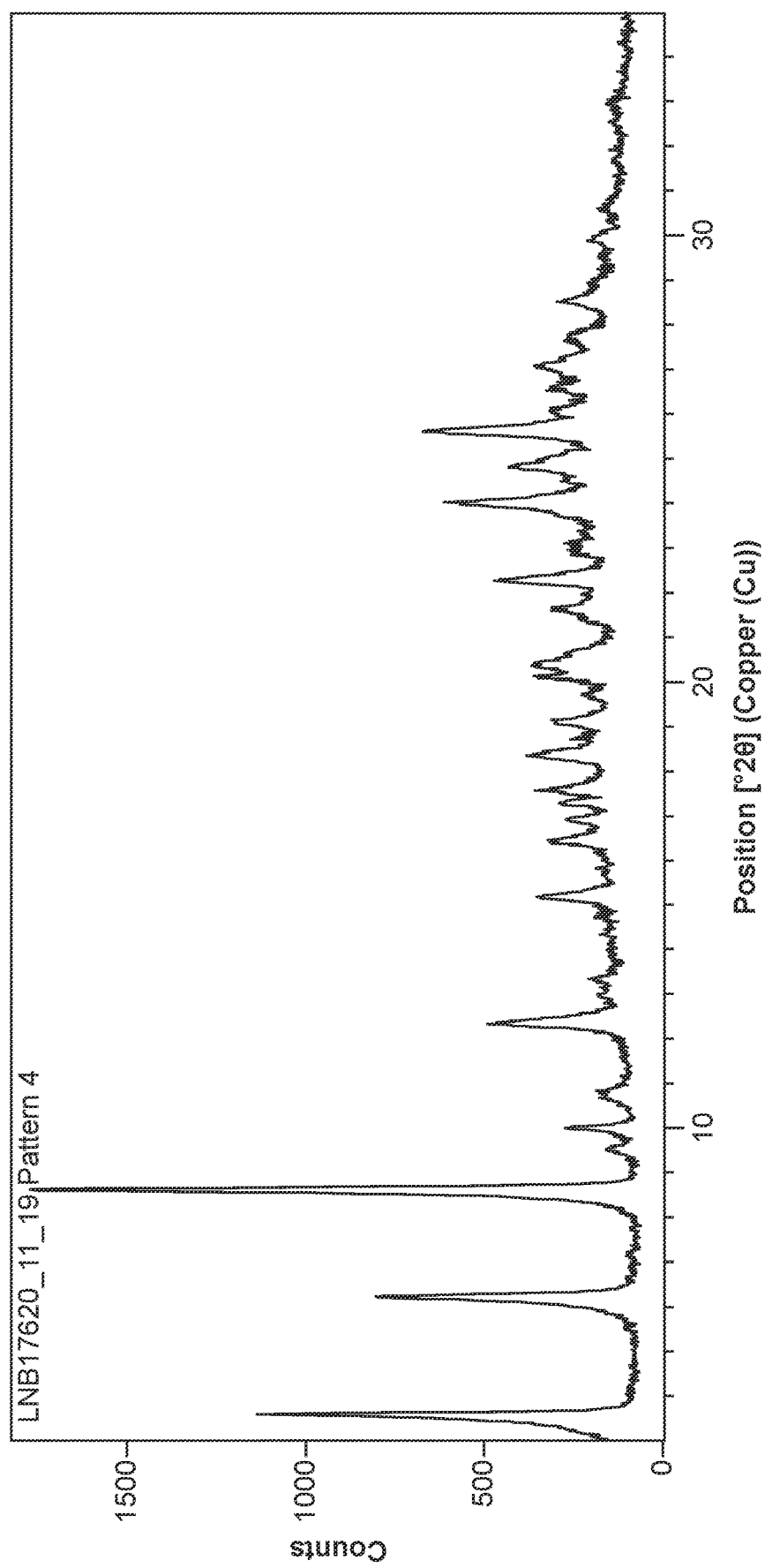
FIG. 8 is an X-ray powder diffractogram of Compound I dihydrochloride Form 4.

The present disclosure provides, in some embodiments, a crystalline form (2S,3R,11bS)-2-(((R)-6,7-dimethoxy-1,2,3,4-tetrahydroisoquinolin-1-yl)methyl)-3-ethyl-9,10-dimethoxy-1,3,4,6,7,11b-hexahydro-2H-pyrido[2,1-a]isoquinoline dihydrochloride ("Compound I dihydrochloride Form 4" or "Form 4") characterized by an X-ray powder diffractogram comprising the following peaks: 3.6, 6.2, and 8.6 °2θ±0.2 °2θ, as determined on a diffractometer using Cu-Kα radiation. In some embodiments, the diffractogram of Compound I dihydrochloride Form 4 further comprises one or more peaks at: 24.0 or 25.6 °2θ±0.2 °2θ. In some embodiments, Compound I dihydrochloride Form 4 is characterized by the X-ray powder diffractogram as substantially shown in FIG. 8.

Figure 9:
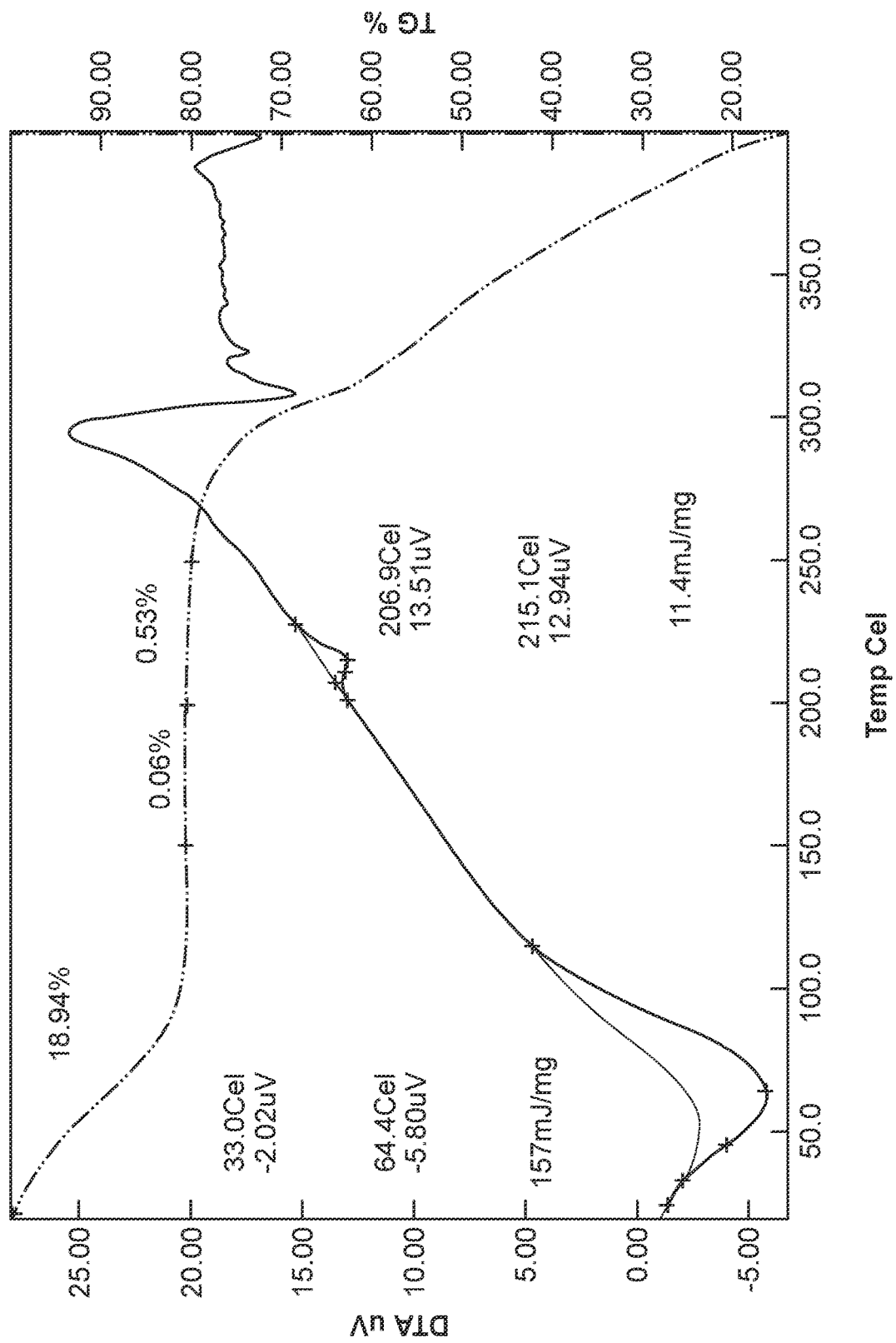
FIG. 9 is a thermogravimetric analysis (TGA) (top line) and a differential thermal analysis (DTA) (bottom line) curve of Compound I dihydrochloride Form 4.

In some embodiments, Compound I dihydrochloride Form 4 is characterized by a differential thermal analysis (DTA) curve that comprises an endotherm at about 33° C. (onset temperature). In some embodiments, the DTA curve of Compound I dihydrochloride Form 4 comprises an additional endotherm at about 207° C. (onset temperature). In some embodiments, Compound I dihydrochloride Form 4 is characterized by the DTA curve as substantially shown in FIG. 9 (bottom line).

In some embodiments, Compound I dihydrochloride Form 4 is characterized by a thermogravimetric analysis (TGA) thermogram showing a weight loss of about 18.9% from the outset to 150° C., followed by weight loss of 0.6% between 150-250° C. In some embodiments, Compound I dihydrochloride Form 4 is characterized by the thermogram as substantially shown in FIG. 9 (top line).

Compound I dihydrochloride Form 5

The present disclosure provides, in some embodiments, a crystalline form (2S,3R,11bS)-2-(((R)-6,7-dimethoxy-1,2,3,4-tetrahydroisoquinolin-1-yl)methyl)-3-ethyl-9,10-dimethoxy-1,3,4,6,7,11b-hexahydro-2H-pyrido[2,1-a]isoquinoline dihydrochloride ("Compound I dihydrochloride Form 5" or "Form 5") characterized by an X-ray powder diffractogram comprising the following peaks: 5.8, 13.0, and 14.2 °2θ±0.2 °2θ, as determined on a diffractometer using Cu-Kα radiation. In some embodiments, the diffractogram of Compound I dihydrochloride Form 5 further comprises one or more peaks at: 16.3, 19.5, or 23.3 °2θ±0.2 °2θ. In some embodiments, Compound I dihydrochloride Form 5 is characterized by the X-ray powder diffractogram as substantially shown in FIG. 10.

Figure 11:
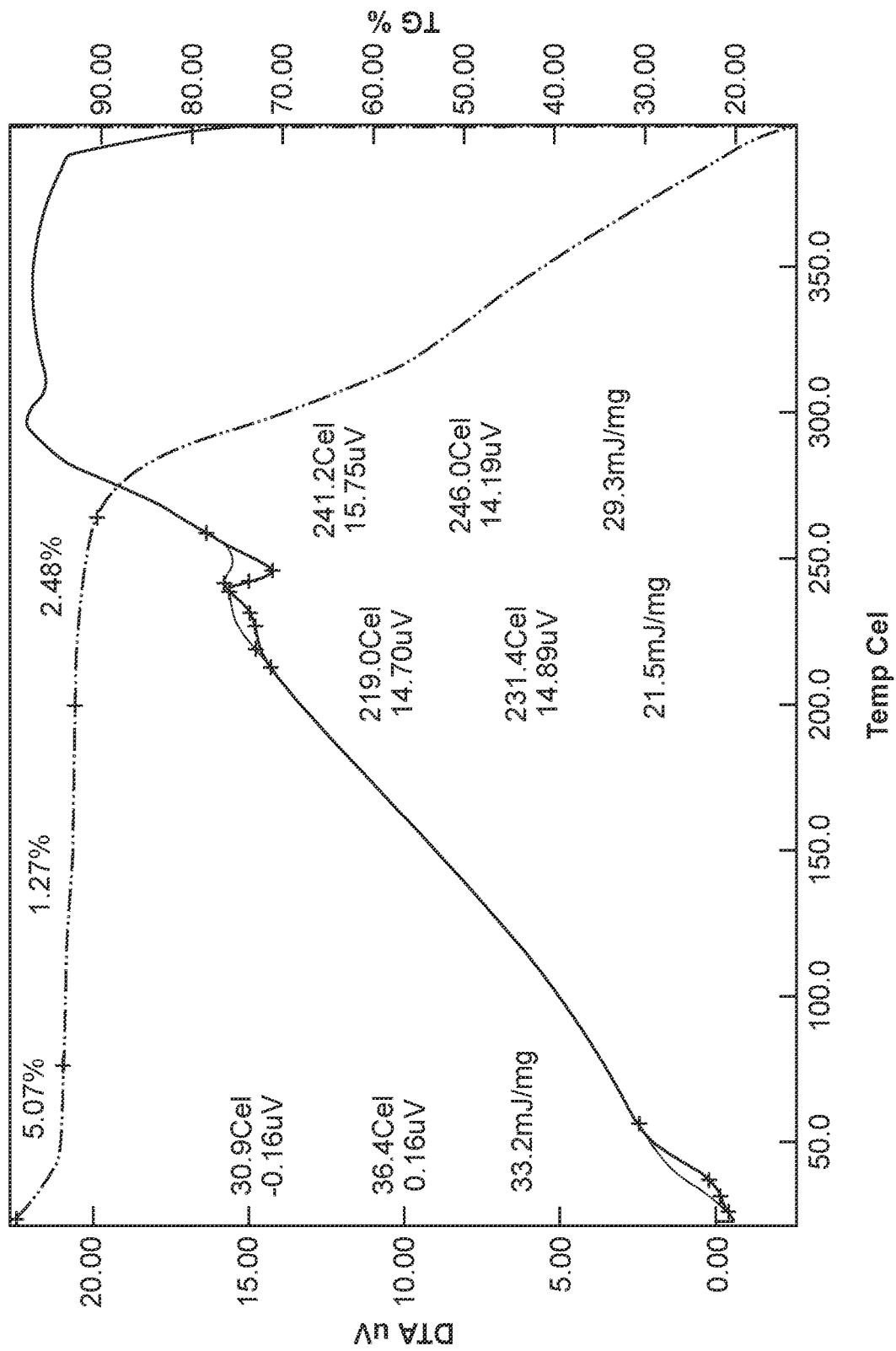
FIG. 11 is a thermogravimetric analysis (TGA) (top line) and a differential thermal analysis (DTA) (bottom line) curve of Compound I dihydrochloride Form 5.

In some embodiments, Compound I dihydrochloride Form 5 is characterized by a differential thermal analysis (DTA) curve that comprises an endotherm at about 31° C. (onset temperature). In some embodiments, the DTA curve of Compound I dihydrochloride Form 5 comprises an additional endotherm at about 219° C. (onset temperature). In some embodiments, the DTA curve of Compound I dihydrochloride Form 5 comprises an additional endotherm at about 241° C. (onset temperature). In some embodiments, Compound I dihydrochloride Form 5 is characterized by the DTA curve as substantially shown in FIG. 11 (bottom line).

In some embodiments, Compound I dihydrochloride Form 5 is characterized by a thermogravimetric analysis (TGA) thermogram showing a weight loss of about 5.10% from the outset to 75° C., followed by weight loss of 1.3% between 75-200° C., with further weight loss of 2.5% between 200-260° C. In some embodiments, Compound I dihydrochloride Form 5 is characterized by the thermogram as substantially shown in FIG. 11 (top line).

Compound I dihydrochloride Form 6

Figure 12:
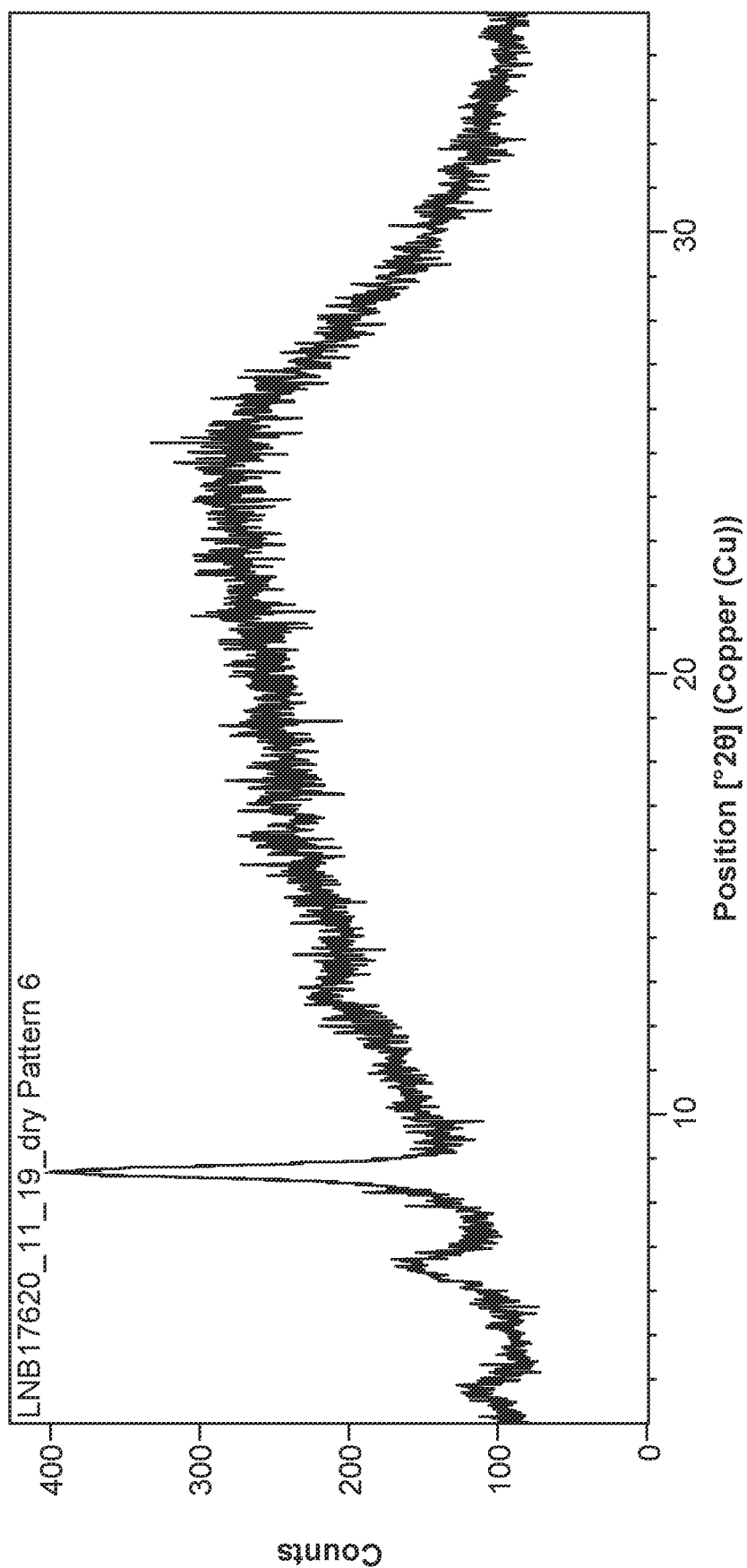
FIG. 12 is an X-ray powder diffractogram of Compound I dihydrochloride Form 6.

The present disclosure provides, in some embodiments, a crystalline form (2S,3R,11bS)-2-(((R)-6,7-dimethoxy-1,2,3,4-tetrahydroisoquinolin-1-yl)methyl)-3-ethyl-9,10-dimethoxy-1,3,4,6,7,11b-hexahydro-2H-pyrido[2,1-a]isoquinoline dihydrochloride ("Compound I dihydrochloride Form 6" or "Form 6") characterized by an X-ray powder diffractogram comprising the following peaks: 8.7, 15.7, and 24.8 °2θ±0.2 °2θ, as determined on a diffractometer using Cu-Kα radiation. In some embodiments, the diffractogram of Compound I dihydrochloride Form 6 further comprises one or more peaks at: 6.6 or 12.0 °2θ±0.2 °2θ. In some embodiments, Compound I dihydrochloride Form 6 is characterized by the X-ray powder diffractogram as substantially shown in FIG. 12.

Compound I dihydrochloride Form 7A

Figure 13:
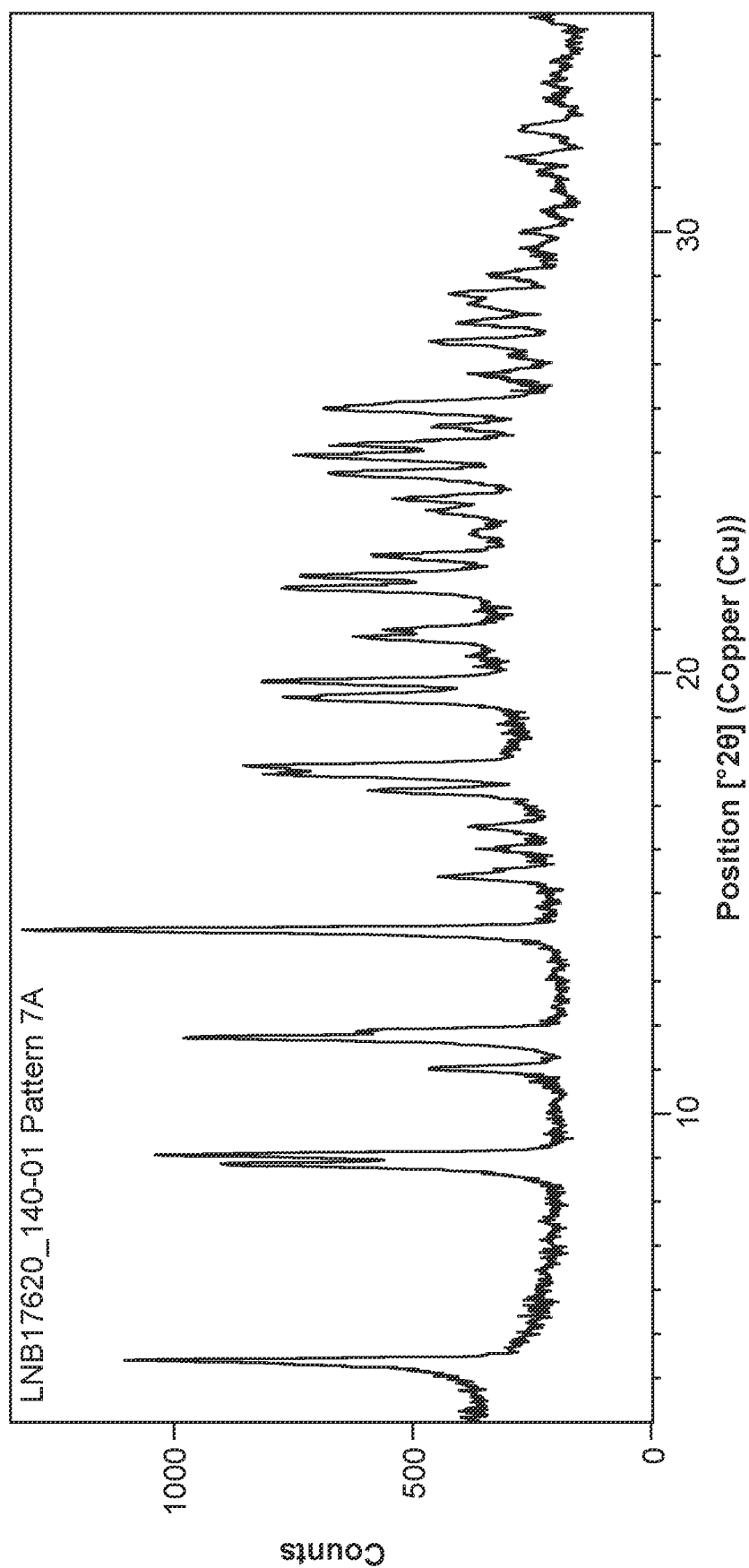
FIG. 13 is an X-ray powder diffractogram of Compound I dihydrochloride Form 7A.

The present disclosure provides, in some embodiments, a crystalline form (2S,3R,11bS)-2-(((R)-6,7-dimethoxy-1,2,3,4-tetrahydroisoquinolin-1-yl)methyl)-3-ethyl-9,10-dimethoxy-1,3,4,6,7,11b-hexahydro-2H-pyrido[2,1-a]isoquinoline dihydrochloride ("Compound I dihydrochloride Form 7A" or "Form 7A") characterized by an X-ray powder diffractogram comprising the following peaks: 4.4, 11.7, 14.2, and 19.4 °2θ±0.2 °2θ, as determined on a diffractometer using Cu-Kα radiation. In some embodiments, the diffractogram of Compound I dihydrochloride Form 7A further comprises one or more peaks at: 8.9 and 9.1 °2θ±0.2 °2θ. In some embodiments, Compound I dihydrochloride Form 7A is characterized by the X-ray powder diffractogram as substantially shown in FIG. 13.

Compound I dihydrochloride Form 8

Figure 14:
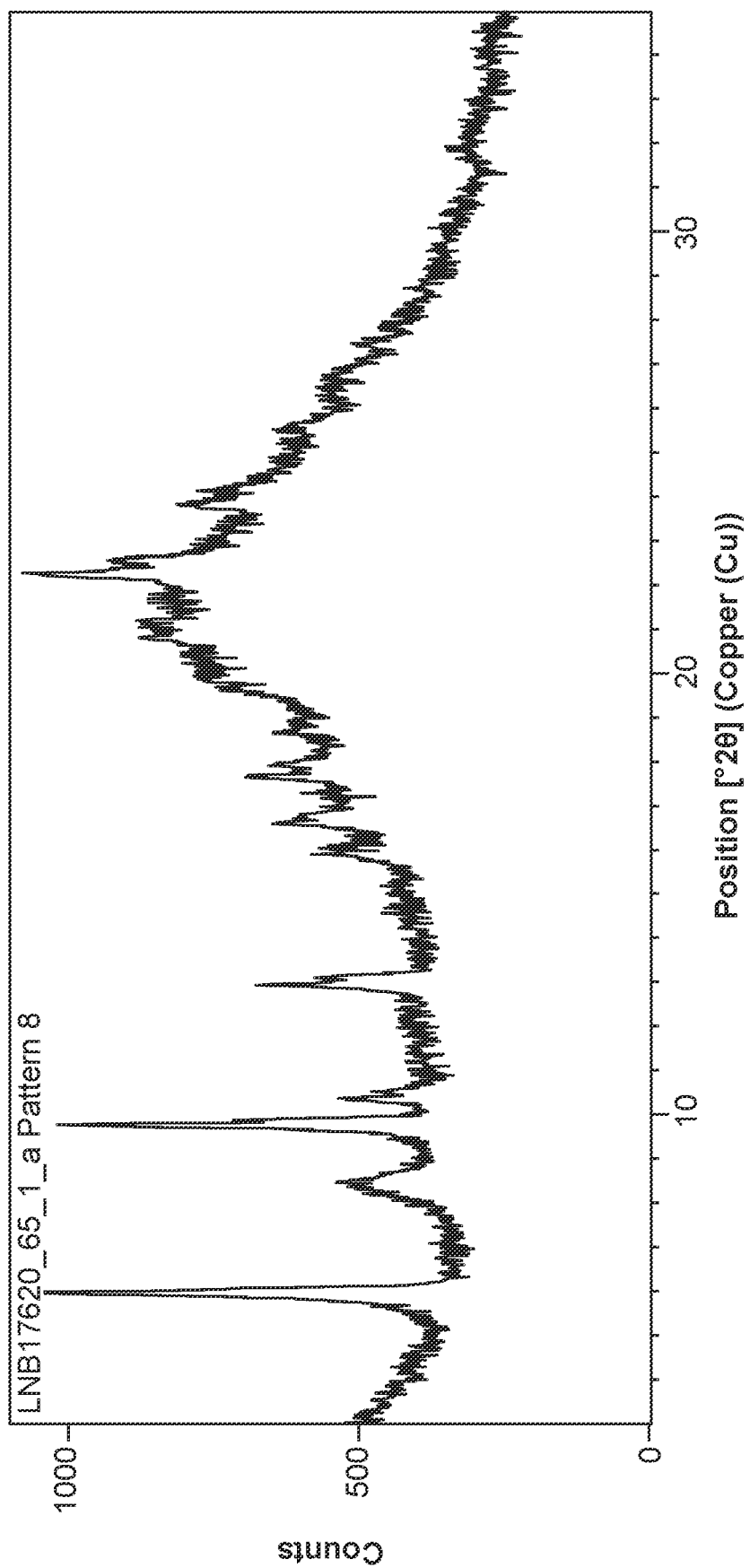
FIG. 14 is an X-ray powder diffractogram of Compound I dihydrochloride Form 8.

The present disclosure provides, in some embodiments, a crystalline form (2S,3R,11bS)-2-(((R)-6,7-dimethoxy-1,2,3,4-tetrahydroisoquinolin-1-yl)methyl)-3-ethyl-9,10-dimethoxy-1,3,4,6,7,11b-hexahydro-2H-pyrido[2,1-a]isoquinoline dihydrochloride ("Compound I dihydrochloride Form 8" or "Form 8") characterized by an X-ray powder diffractogram comprising the following peaks: 6.0, 9.8, 22.2, and 22.6 °2θ±0.2 °2θ, as determined on a diffractometer using Cu-Kα radiation. In some embodiments, the diffractogram of Compound I dihydrochloride Form 8 further comprises one or more peaks at: 17.6, 19.8, 20.8, and 21.1 °2θ±0.2 °2θ. In some embodiments, Compound I dihydrochloride Form 8 is characterized by the X-ray powder diffractogram as substantially shown in FIG. 14.

Pharmaceutical Compositions and Modes of Administration

The solid forms of Compound I dihydrochloride as described herein may be administered in a pharmaceutical composition. Thus, provided herein are pharmaceutical compositions comprising one or more of the crystalline forms of Compound I dihydrochloride described herein and one or more pharmaceutically acceptable vehicles such as carriers, adjuvants and excipients.

Some embodiments are directed to pharmaceutical compositions comprising a therapeutically effective amount of a crystalline form of Compound I dihydrochloride described herein.

In some embodiments, a pharmaceutical composition comprises a crystalline form selected from Compound I dihydrochloride Form 7B, Compound I dihydrochloride Form 1, Compound I dihydrochloride Form 2, Compound I dihydrochloride Form 4, Compound I dihydrochloride Form 5, and Compound I dihydrochloride Form 6; and one or more pharmaceutically acceptable carriers.

In some embodiments, a pharmaceutical composition comprises Compound I dihydrochloride Form 7B and a pharmaceutically acceptable carrier.

Some embodiments are directed to pharmaceutical compositions comprising a crystalline form of Compound I dihydrochloride as described herein and one or more pharmaceutically acceptable carriers. In some embodiments, a pharmaceutical composition comprises Compound I dihydrochloride, wherein at least 95% of Compound I dihydrochloride is in a crystalline form as described herein. In some embodiments, a pharmaceutical composition comprises Compound I dihydrochloride, wherein at least 95% of Compound I dihydrochloride is in Form 7B. In some embodiments, a pharmaceutical composition comprises Compound I dihydrochloride, wherein at least 95% of Compound I dihydrochloride is in Form 1. In some embodiments, a pharmaceutical composition comprises Compound I dihydrochloride, wherein at least 95% of Compound I dihydrochloride is in Form 2. In some embodiments, a pharmaceutical composition comprises Compound I dihydrochloride, wherein at least 95% of Compound I dihydrochloride is in Form 4. In some embodiments, a pharmaceutical composition comprises Compound I dihydrochloride, wherein at least 95% of Compound I dihydrochloride is in Form 5. In some embodiments, a pharmaceutical composition comprises Compound I dihydrochloride, wherein at least 95% of Compound I dihydrochloride is in Form 6.

In some embodiments, a pharmaceutical composition comprises Compound I dihydrochloride, wherein at least 97% of Compound I dihydrochloride is in a crystalline form as described herein. In some embodiments, a pharmaceutical composition comprises Compound I dihydrochloride, wherein at least 97% of Compound I dihydrochloride is in Form 7B. In some embodiments, a pharmaceutical composition comprises Compound I dihydrochloride, wherein at least 97% of Compound I dihydrochloride is in Form 1. In some embodiments, a pharmaceutical composition comprises Compound I dihydrochloride, wherein at least 97% of Compound I dihydrochloride is in Form 2. In some embodiments, a pharmaceutical composition comprises Compound I dihydrochloride, wherein at least 97% of Compound I dihydrochloride is in Form 4. In some embodiments, a pharmaceutical composition comprises Compound I dihydrochloride, wherein at least 97% of Compound I dihydrochloride is in Form 5. In some embodiments, a pharmaceutical composition comprises Compound I dihydrochloride, wherein at least 97% of Compound I dihydrochloride is in Form 6.

In some embodiments, a pharmaceutical composition comprises Compound I dihydrochloride, wherein at least 99% of Compound I dihydrochloride is in a crystalline form as described herein. In some embodiments, a pharmaceutical composition comprises Compound I dihydrochloride, wherein at least 99% of Compound I dihydrochloride is in Form 7B. In some embodiments, a pharmaceutical composition comprises Compound I dihydrochloride, wherein at least 99% of Compound I dihydrochloride is in Form 2. In some embodiments, a pharmaceutical composition comprises Compound I dihydrochloride, wherein at least 99% of Compound I dihydrochloride is in Form 5. In some embodiments, a pharmaceutical composition comprises Compound I dihydrochloride, wherein at least 99% of Compound I dihydrochloride is in Form 1. In some embodiments, a pharmaceutical composition comprises Compound I dihydrochloride, wherein at least 99% of Compound I dihydrochloride is in Form 4. In some embodiments, a pharmaceutical composition comprises Compound I dihydrochloride, wherein at least 99% of Compound I dihydrochloride is in Form 6.

In some embodiments, a pharmaceutical composition comprises Compound I dihydrochloride, wherein at least 99.5% of Compound I dihydrochloride is in a crystalline form as described herein. In some embodiments, a pharmaceutical composition comprises Compound I dihydrochloride, wherein at least 99.5% of Compound I dihydrochloride is in Form 7B. In some embodiments, a pharmaceutical composition comprises Compound I dihydrochloride, wherein at least 99.5% of Compound I dihydrochloride is in Form 2. In some embodiments, a pharmaceutical composition comprises Compound I dihydrochloride, wherein at least 99.5% of Compound I dihydrochloride is in Form 5. In some embodiments, a pharmaceutical composition comprises Compound I dihydrochloride, wherein at least 99.5% of Compound I dihydrochloride is in Form 1. In some embodiments, a pharmaceutical composition comprises Compound I dihydrochloride, wherein at least 99.5% of Compound I dihydrochloride is in Form 4. In some embodiments, a pharmaceutical composition comprises Compound I dihydrochloride, wherein at least 99.5% of Compound I dihydrochloride is in Form 6.

In some embodiments, a pharmaceutical composition comprises Compound I dihydrochloride, wherein at least 99.9% of Compound I dihydrochloride is in a crystalline form as described herein. In some embodiments, a pharmaceutical composition comprises Compound I dihydrochloride, wherein at least 99.9% of Compound I dihydrochloride is in Form 7B. In some embodiments, a pharmaceutical composition comprises Compound I dihydrochloride, wherein at least 99.9% of Compound I dihydrochloride is in Form 2. In some embodiments, a pharmaceutical composition comprises Compound I dihydrochloride, wherein at least 99.9% of Compound I dihydrochloride is in Form 5. In some embodiments, a pharmaceutical composition comprises Compound I dihydrochloride, wherein at least 99.9% of Compound I dihydrochloride is in Form 1. In some embodiments, a pharmaceutical composition comprises Compound I dihydrochloride, wherein at least 99.9% of Compound I dihydrochloride is in Form 4. In some embodiments, a pharmaceutical composition comprises Compound I dihydrochloride, wherein at least 99.9% of Compound I dihydrochloride is in Form 6.

Some embodiments provide for a pharmaceutical composition as described herein and further comprising one or more additional therapeutic agents as described herein.

Suitable pharmaceutically acceptable vehicles of the pharmaceutical compositions described herein may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modem Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal, and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the solid forms described herein. Administration may be via, for example, capsule or enteric coated tablets. In making the pharmaceutical compositions that include at least one solid form described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one solid form described herein can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein. When referring to these preformulation compositions as homogeneous, the active ingredient may be dispersed evenly throughout the composition so that the composition may be readily subdivided into equally effective unit dosage forms such as tablets, pills and capsules.

The tablets or pills of the solid forms described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Treatment Methods and Uses

Provided herein are methods of treating or preventing a viral infection in a subject in need thereof, the method comprising administering to the patient a therapeutically effective amount of a solid form of Compound I dihydrochloride as described herein or a pharmaceutical composition as described herein. Some embodiments provide for a method of treating a viral infection in a subject in need thereof, the method comprising administering to the patient a therapeutically effective amount of a crystalline form as described herein or a pharmaceutical composition as described herein. Additional methods of using the solid forms of emetine are further described in Examples 1-3 of WO 2021/195521, which is hereby incorporated by reference in its entirety.

In some embodiments, the viral infection is caused by Zika virus (ZIKV), Ebola virus (EBOV), Rabies lyssavirus (RABV), cytomegalovirus (CMV), human immunodeficiency virus 1 (HIV-1), influenza A virus, Rift Valley fever virus (RVFV), echovirus 1 (EV1), human metapneumorivus (HMPV), and herpes simplex virus type 2 (HSV-2). In some embodiments, the viral infection is caused by EBOV.

In some embodiments, the viral infection is caused by a coronavirus. In some embodiments, the coronavirus is 229E, NL63, OC43, HKU1, MERS-CoV, SARS-CoV, or SARS-CoV-2. In some embodiments, the coronavirus is MERS-CoV. In some embodiments, the coronavirus is SARS-CoV. In some embodiments, the coronavirus is SARS-CoV-2.

In some embodiments, the viral infection is a Flavivirus infection.

In some embodiments, the Flavivirus infection is Zika virus, West Nile virus, dengue virus (e.g., type 1, 2, 3, or 4), tick-borne encephalitis virus, Japanese encephalitis virus, St, Louis encephalitis virus, or yellow fever virus. In some embodiments, the Flavivirus infection is a Zika virus infection. In some embodiments, the Flavivirus infection is a dengue virus infection.

Provided herein are methods of treating or preventing a viral infection caused by a Flavivirus infection, in a subject in need thereof, the method comprising administering to the patient a therapeutically effective amount of a solid form of Compound I dihydrochloride as described herein or a pharmaceutical composition as described herein.

Provided herein are methods of treating or preventing a viral infection caused by SARS-CoV-2 in a subject in need thereof, comprising administering a therapeutically effective amount of a solid form of Compound I dihydrochloride as described herein or a pharmaceutical composition as described herein. Provided herein are methods of treating or preventing COVID-19 in a subject in need thereof, comprising administering a therapeutically effective amount of a solid form of Compound I dihydrochloride as described herein or a pharmaceutical composition as described herein.

Provided herein are methods of preventing a viral infection caused by SARS-CoV-2 in a subject in need thereof, comprising administering a therapeutically effective amount of a crystalline form of Compound I dihydrochloride as described herein or a pharmaceutical composition as described herein.

Provided herein are methods of preventing COVID-19 in a subject in need thereof, comprising administering a therapeutically effective amount of a crystalline form of Compound I dihydrochloride as described herein or a pharmaceutical composition as described herein.

Provided herein are methods of treating a viral infection in a subject in need thereof, the method comprising administering to the patient a therapeutically effective amount of a crystalline form of Compound I dihydrochloride as described herein or a pharmaceutical composition as described herein, wherein the viral infection is caused by severe acute respiratory syndrome coronavirus 2 (SARS-CoV-2), and wherein the subject does not require hospitalization.

Provided herein are methods of treating a viral infection in a subject in need thereof, the method comprising administering to the patient a therapeutically effective amount of Compound I dihydrochloride Form 7B, wherein the viral infection is caused by severe acute respiratory syndrome coronavirus 2 (SARS-CoV-2), and wherein the subject does not require hospitalization.

Provided herein are methods of treating COVID-19 in a subject in need thereof, comprising administering a therapeutically effective amount of a crystalline form of Compound I dihydrochloride as described herein or a pharmaceutical composition as described herein, and wherein the subject does not require hospitalization.

Provided herein are methods of treating COVID-19 in a subject in need thereof, comprising administering a therapeutically effective amount of Compound I dihydrochloride Form 7B, and wherein the subject does not require hospitalization.

In some embodiments of the methods described herein, the subject does not exhibit severe symptoms of Cytokine Release Syndrome (cytokine storm).

Provided herein are methods of preventing a viral infection caused by SARS-CoV-2 in a subject in need thereof, comprising administering a therapeutically effective amount of a crystalline form of Compound I dihydrochloride as described herein or a pharmaceutical composition as described herein, and wherein the subject is a high-risk, symptomatic adult patient with confirmed COVID-19 infection not requiring hospitalization.

Provided herein are methods of preventing COVID-19 in a subject in need thereof, comprising administering a therapeutically effective amount of a crystalline form of Compound I dihydrochloride as described herein or a pharmaceutical composition as described herein, and wherein the subject is a high-risk, symptomatic adult patient with confirmed COVID-19 infection not requiring hospitalization.

In some embodiments, administration occurs prior to viral infection of the subject.

In some embodiments, methods of preventing a viral infection caused by SARS-CoV-2 or preventing COVID-19 comprise administering a therapeutically effective amount of a crystalline form of Compound I dihydrochloride as described herein as a single dose.

In some embodiments, methods of preventing a viral infection caused by SARS-CoV-2 or preventing COVID-19 comprise administering a booster of a therapeutically effective amount of a crystalline form of Compound I dihydrochloride as described herein. The booster may be administered concurrently or separately and may or may not be equivalent in amount to the first dose.

Provided herein are methods of treating a viral infection in a subject in need thereof, comprising administering a therapeutically effective amount of a crystalline form of Compound I dihydrochloride as described herein, wherein the viral infection is caused by a coronavirus.

In some embodiments, the viral infection is caused by severe acute respiratory syndrome coronavirus 2 (SARS-CoV-2).

Provided herein are methods of treating COVID-19 in a subject in need thereof, comprising administering a therapeutically effective amount of a crystalline form of Compound I dihydrochloride as described herein.

Provided herein are methods of treating a viral infection in a subject in need thereof, comprising administering a therapeutically effective amount of a crystalline form of Compound I dihydrochloride as described herein, wherein:
 the viral infection is caused by severe acute respiratory syndrome coronavirus 2 (SARS-CoV-2);
 the subject does not require hospitalization; and
 the therapeutically effective amount of a crystalline form of Compound I dihydrochloride is about 3 mg to about 65 mg per day.

Also provided herein are methods of treating COVID-19 in a subject in need thereof, comprising administering a therapeutically effective amount of a crystalline form of Compound I dihydrochloride as described herein, wherein:
 the subject does not require hospitalization; and
 the therapeutically effective amount of a crystalline form of Compound I dihydrochloride is about 3 mg to about 65 mg per day.

Also provided herein are methods of treating a viral infection in a subject in need thereof, comprising administering a composition comprising a therapeutically effective amount of a crystalline form of Compound I dihydrochloride and a pharmaceutically acceptable carrier, wherein:
 the viral infection is caused by severe acute respiratory syndrome coronavirus 2 (SARS-CoV-2);
 the subject does not require hospitalization; and
 the therapeutically effective amount of a crystalline form of Compound I dihydrochloride is about 3 mg to about 65 mg per day.

Also provided herein are methods of treating COVID-19 in a subject in need thereof, comprising administering a composition comprising a therapeutically effective amount of a crystalline form of Compound I dihydrochloride and a pharmaceutically acceptable carrier, wherein:
 the subject does not require hospitalization; and
 the therapeutically effective amount of a crystalline form of Compound I dihydrochloride is about 3 mg to about 65 mg per day.

In some embodiments of the methods described herein, the crystalline form of Compound I dihydrochloride is Form 7B. In some embodiments of the methods described herein, the crystalline form of Compound I dihydrochloride is Form 2. In some embodiments of the methods described herein, the crystalline form of Compound I dihydrochloride is Form 5. In some embodiments of the methods described herein, the crystalline form of Compound I dihydrochloride is Form 1. In some embodiments of the methods described herein, the crystalline form of Compound I dihydrochloride is Form 4. In some embodiments of the methods described herein, the crystalline form of Compound I dihydrochloride is Form 6.

In some embodiments, the therapeutically effective amount of a crystalline form of Compound I dihydrochloride is about 1 mg/kg of the subject's body weight to about 1000 mg/kg per day. In some embodiments, the therapeutically effective amount of a crystalline form of Compound I dihydrochloride is about 1 mg/kg of the subject's body weight to about 500 mg/kg per day. In some embodiments, the therapeutically effective amount of a crystalline form of Compound I dihydrochloride is about 1 mg/kg of the subject's body weight to about 250 mg/kg per day. In some embodiments, the therapeutically effective amount of a crystalline form of Compound I dihydrochloride is about 1 mg/kg of the subject's body weight to about 100 mg/kg per day. In some embodiments, the therapeutically effective amount of a crystalline form of Compound I dihydrochloride is about 1 mg/kg of the subject's body weight to about 50 mg/kg per day. In some embodiments, the therapeutically effective amount of a crystalline form of Compound I dihydrochloride is about 1 mg/kg of the subject's body weight to about 10 mg/kg per day. In some embodiments, the therapeutically effective amount of a crystalline form of Compound I dihydrochloride is about 0.1 mg/kg of the subject's body weight to about 1 mg/kg per day. In some embodiments, the therapeutically effective amount of a crystalline form of Compound I dihydrochloride is about 1 mg/kg of the subject's body weight to about 10 mg/kg per day and administered for 10 days. In some embodiments, the therapeutically effective amount of a crystalline form of Compound I dihydrochloride is about 1 mg/kg of the subject's body weight per day and administered for 10 days.

In some embodiments, the therapeutically effective amount of a crystalline form of Compound I dihydrochloride is about 0.1 mg/kg of the subject's body weight per day and administered for more than 1 day. In some embodiments, the therapeutically effective amount of a crystalline form of Compound I dihydrochloride is about 0.1 mg/kg of the subject's body weight per day and is administered after the subject is administered an initial dose of more than 0.1 mg/kg of the subject's body weight. In some embodiments, the therapeutically effective amount of a crystalline form of Compound I dihydrochloride is about 0.01 mg/kg of the subject's body weight to about 0.1 mg/kg of the subject's body weight per day In some embodiments, a crystalline form of Compound I dihydrochloride is administered orally.

In some embodiments, the therapeutically effective amount of a crystalline form of Compound I dihydrochloride is about 1 mg to about 1000 mg per day. In some embodiments, the therapeutically effective amount of a crystalline form of Compound I dihydrochloride is 1 mg to about 500 mg per day. In some embodiments, the therapeutically effective amount of a crystalline form of Compound I dihydrochloride is 1 mg to about 50 mg per day. In some embodiments, the therapeutically effective amount of a crystalline form of Compound I dihydrochloride is 100 mg per day. In some embodiments, the therapeutically effective amount of a crystalline form of Compound I dihydrochloride is 50 mg per day. In some embodiments, the therapeutically effective amount of a crystalline form of Compound I dihydrochloride is 1 mg per day. In some embodiments, the therapeutically effective amount of a crystalline form of Compound I dihydrochloride is about 1 mg to about 70 mg per day. In some embodiments, the therapeutically effective amount of a crystalline form of Compound I dihydrochloride is about 3 mg to about 65 mg per day. In some embodiments, the therapeutically effective amount of a crystalline form of Compound I dihydrochloride is about 5 mg to about 10 mg per day.

In some embodiments, the therapeutically effective amount of a crystalline form of Compound I dihydrochloride is about 10 mg. In some embodiments, the therapeutically effective amount of a crystalline form of Compound I dihydrochloride is about 50 mg. In some embodiments, the therapeutically effective amount of a crystalline form of Compound I dihydrochloride is about 100 mg. In some embodiments, the therapeutically effective amount of a crystalline form of Compound I dihydrochloride is about 150 mg. In some embodiments, the therapeutically effective amount of a crystalline form of Compound I dihydrochloride is about 10 mg to about 175 mg.

In some embodiments, the therapeutically effective amount of a crystalline form of Compound I dihydrochloride is about 65 mg per day. In some embodiments, the therapeutically effective amount of a crystalline form of Compound I dihydrochloride is about 60 mg per day. In some embodiments, the therapeutically effective amount of a crystalline form of Compound I dihydrochloride is about 30 mg per day. In some embodiments, the therapeutically effective amount of a crystalline form of Compound I dihydrochloride is about 10 mg per day. In some embodiments, the therapeutically effective amount of a crystalline form of Compound I dihydrochloride is about 5 mg per day.

In some embodiments, the therapeutically effective amount of a crystalline form of Compound I dihydrochloride is about 10 mg per day for 5 days, 6 days, 7 days, 8 days, 9 days, or 10 days.

In some embodiments, the therapeutically effective amount of a crystalline form of Compound I dihydrochloride is about 60 mg per day and is administered to the subject in need thereof for at least 1 day and up to 10 days. In some embodiments, about 60 mg per day of a crystalline form of Compound I dihydrochloride is administered to the subject in need thereof for less than 7 days, less than 6 days, or less than 5 days.

In some embodiments, about 10 mg per day of a crystalline form of Compound I dihydrochloride is administered to the subject in need thereof for 1 day, followed by about 5 mg per day of a crystalline form of Compound I dihydrochloride for up to 13 days, up to 10 days, up to 9 days, or up to 8 days.

In some embodiments, the subject is a human. In some embodiments, the subject is a human of at least 18 years of age. In some embodiments, the subject is a human less than 18 years of age.

In some embodiments, the subject does not require hospitalization. In some embodiments, the subject does not require admission to a hospital. In some embodiments, the subject has a length of stay in a hospital of less than 1 day. In some embodiments, the subject does not require intensive care unit (ICU) admission. In some embodiments, the subject does not require mechanical ventilation. In some embodiments, the subject does not require supplemental oxygen. In some embodiments, the subject exhibits an oxygen saturation level of between about 90% to about 100%. In some embodiments, the subject exhibits oxygen saturation levels of between about 95% to about 100%. In some embodiments, the subject exhibits oxygen saturation levels below about 95% but does not exhibit difficulty breathing. In some embodiments, the subject exhibits mild to moderate symptoms. Such symptoms include but are not limited to fever, cough, shortness of breath or difficulty breathing, tiredness, aches, runny nose, sore throat, and/or loss of smell or taste. In some embodiments, the subject is a high-risk, symptomatic adult patient with confirmed COVID-19 infection not requiring hospitalization. In some embodiments, a high-risk patient is over 60 years old and/or has hypertension, has diabetes, has a pulmonary dysfunction, has an immune system disorder, or a combination thereof.

It has been suggested that SARS-CoV-2 enters cells through angiotensin-converting enzyme 2 (ACE2). Lung tissue consequently has become the main invasion target of the SARS-CoV-2 virus as the lung expresses high levels of ACE2. After the virus enters the lungs, tissue-associated macrophages initially respond to the virus via a class of receptors known as pattern-recognition receptors. Once macrophages are activated, a variety of cytokines are released, resulting in the infiltration and activation of multiple other immune cells. These immune cells attack the lung tissue indiscriminately, leading to respiratory distress.

Cytokine release syndrome (CRS) is a form of systemic inflammatory response syndrome that occurs when large numbers of white blood cells are activated and release inflammatory cytokines, which in turn activate even more white blood cells. Severe cases have been called cytokine storms. CRS occurs when large numbers of white blood cells, including B cells, T cells, natural killer cells, macrophages, dendritic cells, and monocytes are activated and release inflammatory cytokines, which in turn activate yet more white blood cells. This can occur when the immune system is fighting pathogens, as cytokines signal immune cells such as T-cells and macrophages to travel to the site of infection. In addition, cytokines activate those cells, stimulating them to produce more cytokines. Symptoms of CRS include fever, fatigue, loss of appetite, muscle and joint pain, nausea, vomiting, diarrhea, rashes, fast breathing, rapid heartbeat, low blood pressure, seizures, headache, confusion, delirium, hallucinations, tremor, and loss of coordination. Cytokine storm may be the probable reason for many deaths during the 2019-2020 COVID-19 pandemic.

Thus, in some embodiments, the subject has been exposed to SARS-CoV-2 but does not exhibit symptoms of CRS. In some embodiments, the subject is infected with SARS-CoV-2 but does not exhibit symptoms of CRS. In some embodiments, the subject does not exhibit severe symptoms of CRS (cytokine storm).

In some embodiments, the subject requires hospitalization. In some embodiments, the subject requires admission to a hospital. In some embodiments, the subject has a length of stay in a hospital of greater than 1 day. In some embodiments, the subject requires intensive care unit (ICU) admission. In some embodiments, the subject requires mechanical ventilation. In some embodiments, the subject requires supplemental oxygen. In some embodiments, the subject exhibits an oxygen saturation level of less than about 90%. In some embodiments, the subject exhibits an oxygen saturation level of between about 50% to about 95%. In some embodiments, the subject exhibits severe symptoms. Such symptoms include but are not limited to trouble breathing, chest pain or pressure, confusion or inability to arouse, and/or blue lips or face. In some embodiments, the subject exhibits severe symptoms of CRS (cytokine storm).

In some embodiments, methods provided herein further comprise administering an additional therapeutic agent. In some embodiments, the additional therapeutic agent is administered simultaneously, prior, or after administration of a crystalline form of Compound I dihydrochloride.

In some embodiments, the additional therapeutic agent is an antiparasitic agent.

In some embodiments, the antiparasitic agent is chloroquine, hydroxychloroquine sulfate, mefloquine, or amodiaquine. In some embodiments, the antiparasitic agent is chloroquine or hydroxychloroquine. In some embodiments, the antiparasitic agent is chloroquine. In some embodiments, the antiparasitic agent is hydroxychloroquine.

In some embodiments, the additional therapeutic agent is an antibiotic. Non-limiting examples of an antibiotic include monesin sodium, oligomycin, and dihydrocelastryl diacetate. In some embodiments, the antibiotic is azithromycin.

In some embodiments, the additional therapeutic agent is a corticosteroid. Non-limiting examples of corticosteroids include prednisone, bethamethasone, hydrocortisone, dexamethasone, fludrocortisone, and the like. In some embodiments, the additional therapeutic agent is dexamethasone.

In some embodiments, the additional therapeutic agent is a niclosamide, an emricasan compound, a cyclin-dependent kinase (CDK) inhibitor (including but not limited to palbociclib, ribociclib, and abemaciclib), or a proteasome inhibitor (including but not limited to bortzomib, carfilzomib, and ixazomib).

In some embodiments, the additional therapeutic agent is teriflunomide, hydroxocobalamin, ensulizole, tenonitrozole, isoliquiritigenin, nitazoxanide, febuxostat, leflunomide, vidofludimus, SB-366791, emodin, diphenyl isophthalate, benzoylpas, fenobam, indobufen, 2-(2H-Benzotriazol-2-yl)-4-methylphenol, tiaprofenic acid, flufenamic acid, vitamin B12, cinanserin, 5-Nitro-2-(3-phenylpropylamino)benzoic acid, veliflapon, thiabendazole, SIB 1893, anethole trithione, naringenin, phenazopyridine, fanetizole, terazosin, diacerein, CAY10505, hesperetin, suprofen, ketorolac tromethamine, piperine, pirarubicin, piraxostat, albendazole oxide, tyrphostin AG 494, genistin, fenbufen, apatinib, RITA, BF-170 hydrochloride, OSI-930, tribromsalan, pifexole, formononetin, ebselen, tranilast, benzylparaben, 2-ethoxyethyl-p-methoxycinnamate, baicalein, nemorubicin, rutaecarpine, 2-methyl-6-(phenylethynyl)pyridine (MPEP), 5,7-dihydroxyflavone, vitamin B12, pipofezine, flurbiprofen axetil, 2-amino-6-nitrobenzothiazole, malachite green oxalate, enfenamic acid, fenaminosulf, AS-252424, phenserine, epalrestat, alizarin, dalcetrapib, SN-38, echinomycin, (S)-(+)-camptothecin, BI-2536, 10-hydroxycamptothecin, topotecan, delanzomib, volasertib, ispinesib, paclitaxel, FK-506, AVN-944, digoxin, vincristine, idarubicin, thapsigargin, lexibulin, ixazomib, cephalomannine, mitoxantrone, MLN-2238, demecolcine, vinorelbine, bardoxolone methyl, cycloheximide, actinomycin D, AZD-7762, PF-184, CHIR-124, cyanein, triptolide, KX-01, PF-477736, epirubicin, mycophenolate (mycophenolic acid), daunorubicin, PIK-75, vindesine, torin-2, floxuridine, Go-6976, or OSU-03012.

In some embodiments, the additional therapeutic agent is an antiviral agent.

In some embodiments, the antiviral agent is amantadine, ampligen, umifenovir, baloxavir marboxil, ganciclovir, letermovir, moroxydine, nitazoxanide, oseltamavir, peramivir, pleconaril, rimantadine, or zanamivir.

In some embodiments, the antiviral agent is interferon, ribavirin, adefovir, tenofovir, acyclovir, brivudin, cidofovir, fomivirsen, foscarnet, ganciclovir, penciclovir, amantadine, rimantadine, lopinavir, ritonavir, zanamivir, darunavir, cobicistat, sofosbuvir, or a combination thereof.

In some embodiments, the antiviral agent is remdesivir or a pharmaceutically acceptable salt thereof. In some embodiments, the antiviral agent is remdesivir. In some embodiments, the antiviral agent is favipiravir or a pharmaceutically acceptable salt thereof. In some embodiments, the antiviral agent is favipiravir.

In some embodiments, the antiviral agent is a broad-spectrum inhibitor of a coronavirus. Non-limiting examples of a broad-spectrum inhibitor of a coronavirus are lycorine, mycophenolate mofetil, phenazopyridine, mycophenolic acid, pyrvinium pamoate, monensin sodium, cycloheximide, cetylpyridinium chloride, oligomycin, promazine, diperodon, dihydrocelastryl diacetate, tetrandrine, pristimerin, and chloroquine.

In some embodiments, the antiviral agent is a broad-spectrum inhibitor of a flavivirus. Non-limiting examples of a broad-spectrum inhibitor of a flavivirus are palmatine, nelfinavir, BCX4430, ST-610, ST-148, lycorine, NSC12155, celgosivir, cyclosporine, lovastatin, eforrnithine, dasatinib, fenretinidie, chloroquine, nitazoxanide, tizoxanide, bromocriptine, and ivermetcin.

In some embodiments, the antiviral agent is a protease inhibitor. Non-limiting examples of protease inhibitors include Paxlovid (PF-07321332), camostat mesylate, nafamostat mesylate, ONO 5334, MDL 28170, apilimod, and other agents that act as viral protease inhibitors. In some embodiments, the additional therapeutic agent is Paxlovid (PF-07321332), or a combination of Paxlovid (PF-07321332) and ritonavir. In some embodiments, the additional therapeutic agent is camostat, or a combination of camostat and trans-epoxysuccinyl-L-leucylamindo-3-methylbutane ethyl ester.

In some embodiments, the antiviral agent is a mutagenic ribonucleoside analog. In some embodiments, the mutagenic ribonucleoside analog is molnupiravir.

In some embodiments, the additional therapeutic agent is an agent that can inhibit an inflammatory response. In some embodiments, such an agent may be useful for controlling a cytokine storm. Non-limiting examples of such agents include sphingosine 1-phosphate receptor 1 modulators (i.e. ozanimod, fingolimod, etc.), COX inhibitors (i.e., mesalamine, celecoxib, etc.), CCR2 inhibitor (PF-041789-3), anti-TNF agents, statins (i.e. simvastatin), OX40-Ig fusion proteins, and PPARα/PPARγ agonists i.e. gemfibrozil, pioglitazone, rosiglitazone, 15d-PGJ2, ciglitazone, troglitazone, etc.). In some embodiments, the agent useful for controlling a cytokine storm is ozanimod or fingolimod.

In some embodiments, the additional therapeutic agent is an anti-IL-6 therapeutic agent. Non-limiting examples of an anti-IL-6 therapeutic agent include tocilizumab, sarilumab, siltuximab, and other agents that target the IL-6 receptor.

In some embodiments, the additional therapeutic agent is an anti-IL-1 therapeutic agent. Non-limiting examples of an anti-IL-1 therapeutic agent include anakinra, canakinumab, and other agents that target the IL-1 receptor. In some embodiments, the additional therapeutic agent is anakinra, or a combination of anakinra and emapalumab.

In some embodiments, the additional therapeutic agent is colchicine.

In some embodiments, the additional therapeutic agent is nitazoxanide.

In some embodiments, the additional therapeutic agent is bamlanivimab. In some embodiments, the additional therapeutic agent is baricitinib or a combination of baricitinib and remdesivir.

In some embodiments, the additional therapeutic agent is casirivimab, imdevimab, or a combination thereof (formerly REGN-COV2).

In some embodiments, the additional therapeutic agent is casirivimab, imdevimab, a combination of casirivimab and imdevimab, baricitinib, tofacitinib, ruxolitinib, eculizumab, remdesivir, PTC299, PRO140 (leronlimab), LY-CoV555 (bamlanivimab), lenzilumab, namilumab, ivermectin, aviptadil (RLF-100), metformin, AT-527, tocilizumab, niclosamide, famotidine, lopinavir-ritonavir (kaletra), inflix- imab, AZD7442 (combination of tixagevimad and cilgavi- mab), abivertinib CT-P59, heparin, GSK4182136, JS016, sarilumab, CD24Fc, adalimumab, STI-1499, dexametha- sone, PB1046, galidesivir, bucillamine, PF-07304814 (PF- 00835321), apixaban, ianadelumab, hydrocortisone, canakinumab, colichicine, BLD-2660, favilavir-avifavir (avigan), gelsolin, MK-4482, TXA127, apilimod dimesy- late, SAR443122, INOpulse, ABX464, AdMSCs, losmapi- mod, mavrilimumab, acalabrutinib, ibrutinib, zanubrutinib, gimsilumab, otilimab, dapagliflozin, ravulizumab, or a com- bination thereof.

In some embodiments, the additional therapeutic agent is fluvoxamine.

In some embodiments, the additional therapeutic agent is AR-12, resveratrol, or curcumin.

In some embodiments, methods provided herein further comprise administering ivermectin.

In some embodiments, methods provided herein further comprise administering to the subject convalescent plasma.

Provided herein are methods of treating a viral infection in a subject in need thereof, comprising administering a therapeutically effective amount of a crystalline form of Compound I dihydrochloride and a therapeutically effective amount of remdesivir, or a pharmaceutically acceptable salt thereof, wherein the viral infection is caused by severe acute respiratory syndrome coronavirus 2 (SARS-CoV-2).

Provided herein are methods of treating a viral infection in a subject in need thereof, comprising administering a therapeutically effective amount of Compound I dihydro- chloride Form 7B and a therapeutically effective amount of remdesivir, or a pharmaceutically acceptable salt thereof, wherein the viral infection is caused by severe acute respi- ratory syndrome coronavirus 2 (SARS-CoV-2).

Also provided herein are compositions comprising a therapeutically effective amount of a crystalline form of Compound I dihydrochloride and a therapeutically effective amount of remdesivir, or a pharmaceutically acceptable salt thereof.

Also provided herein are compositions comprising a therapeutically effective amount of Compound I dihydro- chloride Form 7B and a therapeutically effective amount of remdesivir, or a pharmaceutically acceptable salt thereof.

Also provided herein are methods of treating COVID-19 in a subject in need thereof, comprising administering a therapeutically effective amount of a crystalline form of Compound I dihydrochloride and a therapeutically effective amount of remdesivir, or a pharmaceutically acceptable salt thereof.

Also provided herein are methods of treating COVID-19 in a subject in need thereof, comprising administering a therapeutically effective amount of Compound I dihydro- chloride Form 7B and a therapeutically effective amount of remdesivir, or a pharmaceutically acceptable salt thereof.

Also provided herein are methods of treating COVID-19 in a subject in need thereof, comprising administering a therapeutically effective amount of a crystalline form of Compound I dihydrochloride and a therapeutically effective amount of remdesivir, or a pharmaceutically acceptable salt thereof, wherein the subject does not require hospitalization.

Also provided herein are methods of treating COVID-19 in a subject in need thereof, comprising administering a therapeutically effective amount of a crystalline form of Compound I dihydrochloride and a therapeutically effective amount of remdesivir, or a pharmaceutically acceptable salt thereof, wherein the subject is a high-risk, symptomatic adult patient with confirmed COVID-19 infection not requir- ing hospitalization.

Provided herein are methods of treating a viral infection in a subject in need thereof, comprising administering a therapeutically effective amount of a crystalline form of Compound I dihydrochloride and a therapeutically effective amount of an agent useful for controlling a cytokine storm, or a pharmaceutically acceptable salt thereof, wherein the viral infection is caused by severe acute respiratory syn- drome coronavirus 2 (SARS-CoV-2).

Also provided herein are compositions comprising a therapeutically effective amount of a crystalline form of Compound I dihydrochloride and a therapeutically effective amount of an agent useful for controlling a cytokine storm, or a pharmaceutically acceptable salt thereof.

Also provided herein are methods of treating COVID-19 in a subject in need thereof, comprising administering a therapeutically effective amount of a crystalline form of Compound I dihydrochloride and a therapeutically effective amount of an agent for controlling a cytokine storm, or a pharmaceutically acceptable salt thereof.

Also provided herein are methods of treating COVID-19 in a subject in need thereof, comprising administering a therapeutically effective amount of a crystalline form of Compound I dihydrochloride and a therapeutically effective amount of an agent for controlling a cytokine storm, or a pharmaceutically acceptable salt thereof, wherein the sub- ject does not require hospitalization.

Also provided herein are methods of treating COVID-19 in a subject in need thereof, comprising administering a therapeutically effective amount of a crystalline form of Compound I dihydrochloride and a therapeutically effective amount of an agent for controlling a cytokine storm, or a pharmaceutically acceptable salt thereof, wherein the sub- ject is a high-risk, symptomatic adult patient with confirmed COVID-19 infection not requiring hospitalization.

Provided herein are methods of preventing a viral infec- tion caused by SARS-CoV-2 in a subject in need thereof, comprising administering a therapeutically effective amount of a crystalline form of Compound I dihydrochloride and a therapeutically effective amount of remdesivir, or a phar- maceutically acceptable salt thereof.

Provided herein are methods of preventing a viral infec- tion caused by SARS-CoV-2 in a subject in need thereof, comprising administering a therapeutically effective amount of Compound I dihydrochloride Form 7B and a therapeuti- cally effective amount of remdesivir, or a pharmaceutically acceptable salt thereof.

Provided herein are methods of preventing COVID-19 in a subject in need thereof, comprising administering a thera- peutically effective amount of a crystalline form of Com- pound I dihydrochloride and a therapeutically effective amount of remdesivir, or a pharmaceutically acceptable salt thereof.

Provided herein are methods of preventing COVID-19 in a subject in need thereof, comprising administering a thera- peutically effective amount of Compound I dihydrochloride Form 7B and a therapeutically effective amount of remde- sivir, or a pharmaceutically acceptable salt thereof.

Provided herein are methods of preventing a viral infec- tion caused by SARS-CoV-2 in a subject in need thereof, comprising administering a therapeutically effective amount of a crystalline form of Compound I dihydrochloride and a therapeutically effective amount of remdesivir, or a pharmaceutically acceptable salt thereof, wherein the subject is a high-risk, symptomatic adult patient with confirmed COVID-19 infection not requiring hospitalization.

Provided herein are methods of preventing COVID-19 in a subject in need thereof, comprising administering a therapeutically effective amount of a crystalline form of Compound I dihydrochloride and a therapeutically effective amount of remdesivir, or a pharmaceutically acceptable salt thereof, wherein the subject is a high-risk, symptomatic adult patient with confirmed COVID-19 infection not requiring hospitalization.

It is understood that modifications which do not substantially affect the activity of the various embodiments of this disclosure are also included within the definition of the disclosure provided herein. Accordingly, the following examples are intended to illustrate but not limit the present disclosure.

EXAMPLES

Instrumental Techniques

X-Ray Powder Diffraction

For XRPD analyses provided herein, a PANalytical X'pert pro with PIXcel detector X-ray powder diffractometer was used, and the XRPD parameters used are summarized in Table 1.

TABLE 1

Parameters for XRPD Analysis

| Parameters | XRPD (Transmission Mode) |
| --- | --- |
| X-Ray wavelength | Cu, Kα1 (Å): 1.54060; Kα2 (Å): 1.54443 Å; Kβ (Å) = 1.39225 Kα1:Kα2 ratio = 0.5 |
| X-Ray tube setting | 40 kV, 40 mA |
| Scan range (°2 TH) | 3°-35° |
| Step size (°2 TH) | 0.0130° |
| Step time | 18.87 s |

Thermogravimetric Analysis and Differential Scanning Calorimetry

TGA/DSC was performed using a TA Instruments Discovery SDT 650 Auto-Simultaneous DSC. Detailed parameters used are listed in Table 2.

TABLE 2

Parameters for TGA and DSC Analysis

| Parameters | TGA/DSC |
| --- | --- |
| Sample pan | Aluminum, open |
| Temperature | 30° C.-400° C. |
| Heating rate | 10° C./min |
| Purge gas | $N_2$, flow rate of 200 cm³/min |

Thermogravimetric Analysis and Differential Thermal Analysis

TGA/DTA was performed using a simultaneous thermogravimetric/differential thermal analyzer. Detailed parameters used are listed in Table 3.

TABLE 3

Parameters for TGA and DTA Analysis

| Parameters | TGA/DTA |
| --- | --- |
| Sample pan | Aluminum, open |
| Temperature | 30° C.-400° C. |

TABLE 3-continued

Parameters for TGA and DTA Analysis

| Parameters | TGA/DTA |
| --- | --- |
| Heating rate | 10° C./min |
| Purge gas | $N_2$, flow rate of 300 cm³/min |

Dynamic Vapor Sorption

DVS was measured via a SMS (Surface Measurement Systems) DVS Intrinsic or DVS Advantage dynamic vapor sorption balance. Detailed parameters used are listed in Table 4.

TABLE 4

Parameters for DVS Analysis

| Parameters | DVS |
| --- | --- |
| Temperature | 25° C. |
| Sample size | 10~15 mg |
| dm/dt | 0.004%/min |
| Minimum step length | 30 min |
| Maximum step length | 500 min |
| RH range | 0% RH to 90% RH |
| RH step size | 10% RH from 40% RH to 90% RH |
| | 10% RH from 90% RH to 0% RH |

Example 1. Characterization of Form 1 and Amorphous Compound I Dihydrochloride

Compound I Dihydrochloride Form 1

Compound I dihydrochloride Form 1 is a commercially available crystalline salt.

Compound I dihydrochloride Form 1 is crystalline by XRPD (FIG. 3) and can be characterized by an X-ray powder diffractogram comprising the following peaks: 6.2, 10.0, 13.7, and 23.3 °2θ±0.2 °2θ, as determined on a diffractometer using Cu-Kα radiation. Compound I dihydrochloride Form 1 can be further characterized by an X-ray powder diffractogram comprising one or more peaks at: 11.2, 18.7, or 26.1 °2θ±0.2 °2θ.

TG/DSC analysis (FIG. 4) of Compound I dihydrochloride Form 1 showed weight loss of about 11.0% from the outset up to 115° C., followed by loss of about 1.10% between 115-240° C. An endothermic event was associated with the initial mass loss, with onset at about 61° C. and peak at about 77° C. This was followed by an endothermic event with onset at about 206° C. and peak at about 221° C., prior to the onset of decomposition.

Amorphous Compound I Dihydrochloride

Figure 15:
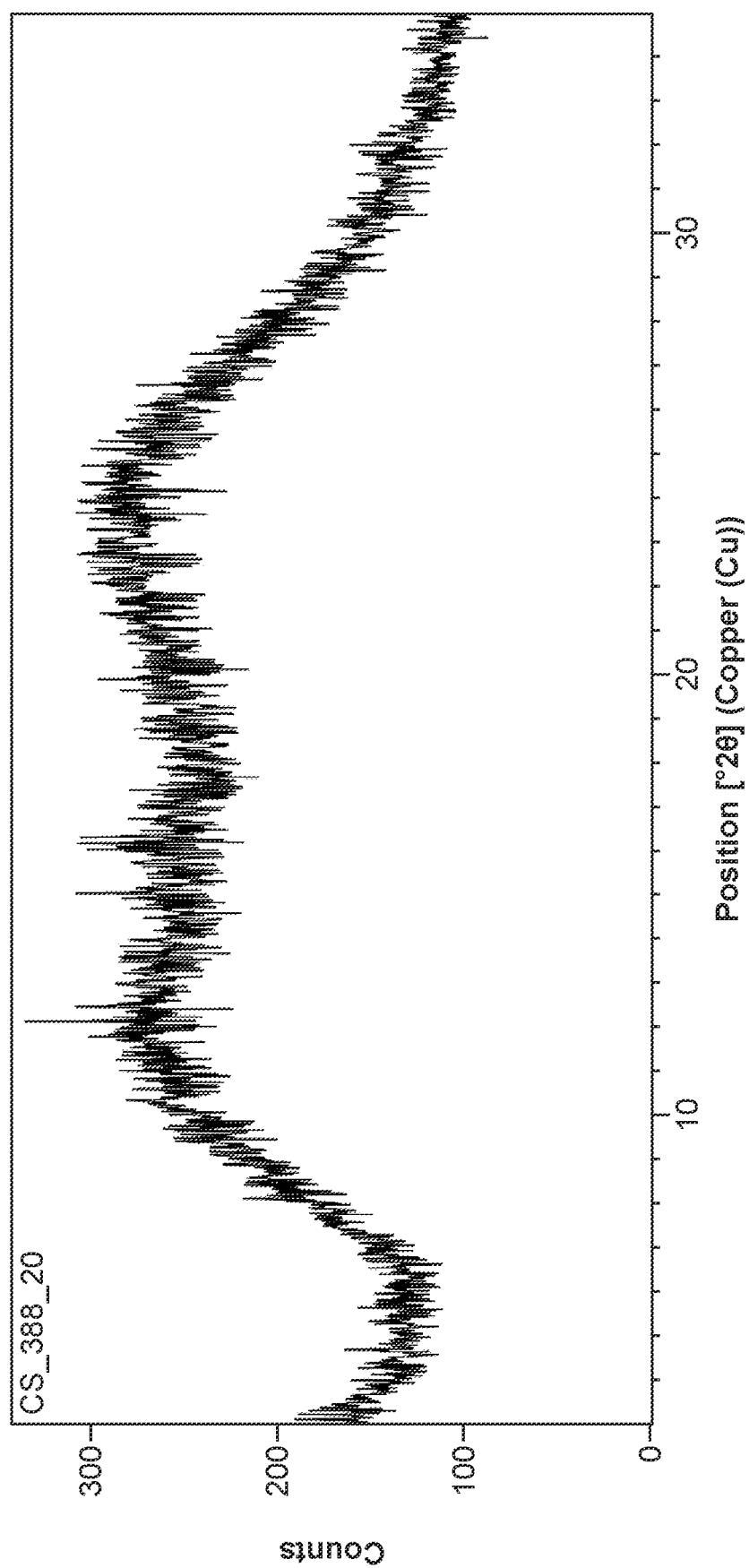
FIG. 15 is an X-ray powder diffractogram of amorphous Compound I dihydrochloride.

Amorphous Compound I dihydrochloride is a commercially available solid and can be characterized by XRPD as shown in FIG. 15.

Figure 16:
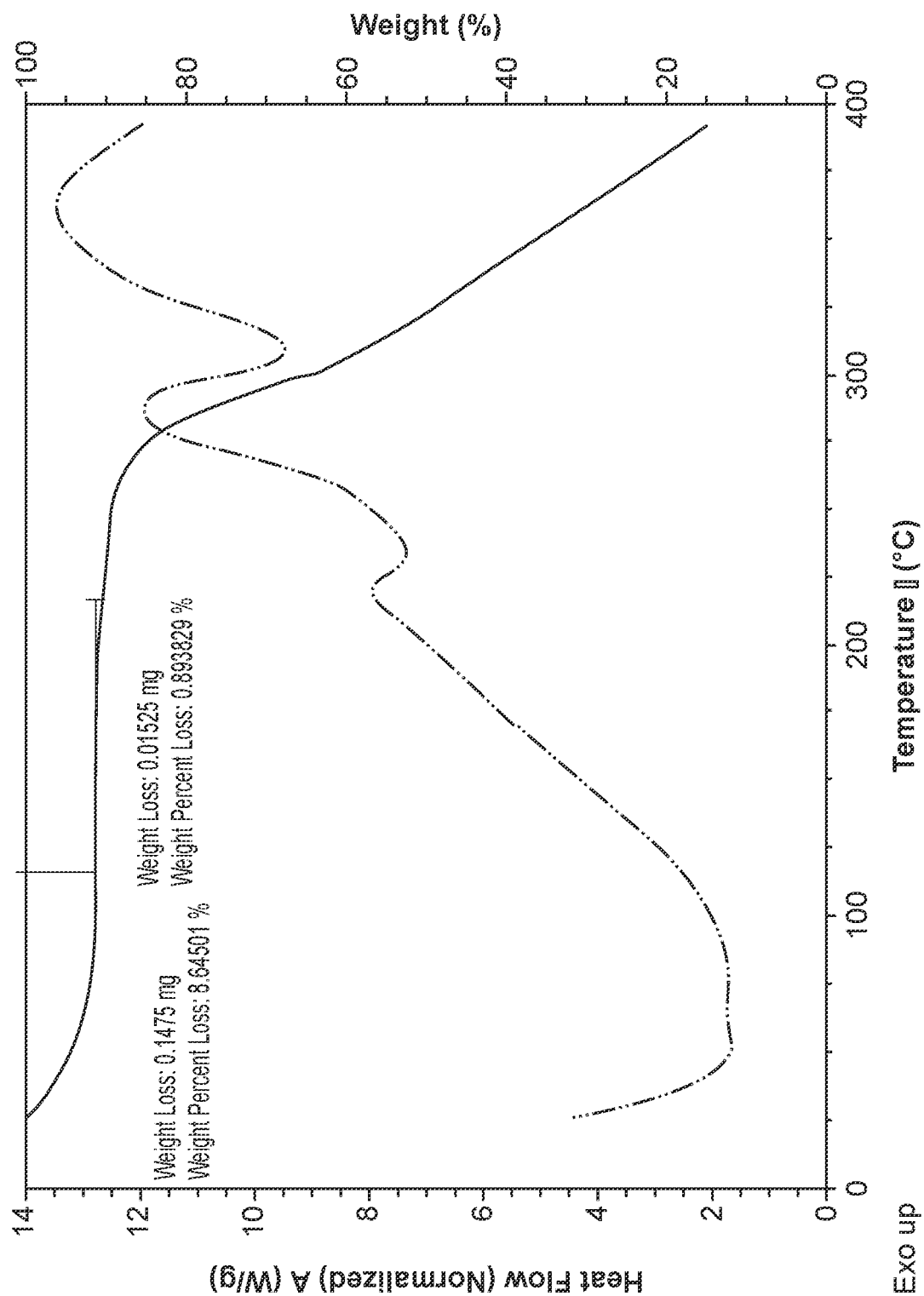
FIG. 16 is a thermogravimetric analysis (TGA) (top line) and a differential scanning calorimeter (DSC) (bottom line) curve of amorphous Compound I dihydrochloride.

TG/DSC analysis of amorphous Compound I dihydrochloride (FIG. 16) showed weight loss of about 8.6% from the outset up to 115° C., followed by loss of about 0.9% between 115-215° C. No significant thermal events were observed prior to the onset of decomposition.

Example 2. Solubility Screening

Approximate solubility values for amorphous Compound I dihydrochloride in 24 solvent systems was estimated by a solvent addition technique (Table 5).

The following procedure was used for the study:

Approximately 20 mg of material was weighed out into 24×2 mL push-cap vials.

Each solvent/solvent mixture was added to the appropriate vial in 5 volume aliquots (100 μL) until either no more solvent could be added or until the material dissolved.

In between additions, the experiments were stirred at 50° C.

Solids were isolated by centrifugation (0.22 μm nylon filter) and analyzed by XRPD; experiments which remained solutions were evaporated at ambient temperature (about 20° C.) under vacuum.

All isolated material was dried under vacuum at about 30° C. for about 19-23 h then re-analyzed by XRPD.

For comparison purposes, the approximate solubility of Compound I dihydrochloride Form 1 was estimated in water, using the same procedure, in solubility screening Experiment 25.

TABLE 5

Solubility Screening

| | | Initial Solvent System | | Additional Solvents | |
|---|---|---|---|---|---|
| Experiment | Compound I dihydrochloride | Solvent System (v/v) | Vol./μL | Anti-Solvent | ASA (1) Vol./μL | ASA (2) Vol./μL |
| 1 | Amorphous | Acetone | 2000 | — | — | — |
| 2 | Amorphous | Anisole | 2000 | — | — | — |
| 3 | Amorphous | t-Butyl methyl ether (tBME) | 2000 | — | — | — |
| 4 | Amorphous | Dimethylformamide (DMF) | 100 | tBME | 250 | — |
| 5 | Amorphous | Dimethylsulfoxide (DMSO) | 100 | tBME, acetone | 250, 200 | — |
| 6 | Amorphous | Ethanol | 100 | — | — | — |
| 7 | Amorphous | Ethyl acetate | 2000 | — | — | — |
| 8 | Amorphous | Heptane | 2000 | — | — | — |
| 9 | Amorphous | Isopropyl acetate | 2000 | — | — | — |
| 10 | Amorphous | Methanol | 100 | — | — | — |
| 11 | Amorphous | Methyl ethyl ketone (MEK) | 2000 | — | — | — |
| 12 | Amorphous | Methyl isobutyl ketone (MiBK) | 2000 | — | — | — |
| 13 | Amorphous | 2-Methyl THF | 2000 | — | — | — |
| 14 | Amorphous | 1-Propanol | 100 | — | — | — |
| 15 | Amorphous | 2-Propanol | 100 | — | — | — |
| 16 | Amorphous | N-Methyl pyrrolidone (NMP) | 100 | tBME | 250 | — |
| 17 | Amorphous | THF | 2000 | — | — | — |
| 18 | Amorphous | Toluene | 2000 | — | — | — |
| 19 | Amorphous | Water | 100 | — | — | — |
| 20 | Amorphous | Acetone:Water 50:50 | 100 | Acetone | 1000 | — |
| 21 | Amorphous | Ethanol:Water 90:10 | 100 | Heptane* | 1000 | 1000 |
| 22 | Amorphous | Ethanol:Water 25:75 | 100 | Acetone | 1000 | 1000 |
| 23 | Amorphous | Methanol:Water 50:50 | 100 | tBME* | 500 | 1000 |
| 24 | Amorphous | 2-Propanol:Water 95:5 | 100 | — | — | — |
| 25 | Form 1 | Water | 400$^a$ | THF* | 1000 | 1000 |

*Acetone used for second ASA.
$^a$No change in fine particles present after addition of 100/μL If 2000 μL of solvent was added without dissolution of the material, solubility was calculated to be below this point.

Experiments were stirred at 50° C. for 1.5-5 h and then cooled at 0.1° C./min to 5° C. and stirred at 5° C. for about 10 h.

Solids (residual and recrystallized) were isolated by centrifugation (0.22 μm nylon filter) and analyzed by XRPD.

Anti-solvent addition (ASA) at 20° C. was carried out on solutions, followed by temperature cycling between 50° C.-5° C. (1 h hold, 0.1° C./min cool, 0.25° C./min ramp) for 20 h.

ASA at 5° C. was carried out on experiments which remained solutions, which were then stirred at 5° C. for 3 h.

Amorphous Compound I dihydrochloride exhibited solubility of >200 mg/mL in alcohols and polar, aprotic solvent systems, including dimethylformamide, dimethylsulfoxide, ethanol, methanol, 1-propanol, 2-propanol, N-methyl-2-pyrrolidone and water. Solubility of >200 mg/mL was also obtained in acetone:water 50:50 v/v, ethanol:water 90:10 and 25:75 v/v, methanol:water 50:50 v/v and 2-propanol:water 95:5 v/v. Amorphous Compound I dihydrochloride had poor solubility (<10 mg/mL) in acetone, anisole, tBME, ethyl acetate, heptane, isopropyl acetate, methylethyl ketone, methylisobutyl ketone, 2-methyl THF, THF and toluene, giving a range of potential anti-solvents.

Slurries were obtained after cooling the experiments in acetone, anisole, tBME, ethanol, ethyl acetate, heptane, isopropyl acetate, methanol, methylethyl ketone, methylisobutyl ketone, 2-methyl THF, 2-propanol, THF, toluene, water and 2-propanol:water 95:5 v/v. Gel was obtained after cooling the experiment carried out using 1-propanol, but converted to solid with the addition of 200 µL of heptane to transfer the material to the centrifuge tube. The experiments carried out in DMF, NMP, acetone:water 50:50 v/v, ethanol:water 90:10 and 25:75 v/v and methanol:water 50:50 v/v remained solutions after cooling to 5° C., while the DMSO experiment was frozen at 5° C. and a solution at 20° C. Anti-solvent addition was carried out to these experiments, with some gum observed in experiments carried out using DMF and NMP. Separation was observed after ASA of tBME to the experiment carried out in DMSO and so acetone was added as a co-solvent to re-homogenize the solution. XRPD analysis of the residual solids indicated that the material remained amorphous after cooling and stirring at 5° C. No changes were observed after drying.

Compound I dihydrochloride Form 1 was observed to dissolve almost completely with the first aliquot of water (solubility of >200 mg/mL at ambient temperature) but small, fine particles remained. Further aliquots of water were added, but no change to these particles were observed and so addition was halted at a concentration of 50 mg/mL and polish filtration carried out prior to cooling.

The isolated solid products from cooling and/or anti-solvent addition in the solubility screening experiments were identified as amorphous Compound I dihydrochloride by XRPD, other than the isolated crystalline products described below:

Compound I Dihydrochloride Form 2

From solubility screening Experiment 6, a stirred solution of approximately 20 mg of amorphous Compound I dihydrochloride in approximately 100 µL of ethanol at 50° C. was cooled at a rate of 0.1° C./min to 5° C. and was stirred for 10 h. Upon cooling, a thick slurry formed. The solids were isolated by centrifugation (0.22 µm nylon filter) and dried under vacuum at about 30° C. for about 19-23 h. The isolated crystalline solid was deemed to be Compound I dihydrochloride Form 2.

Compound I dihydrochloride Form 2 is crystalline by XRPD (FIG. 5) and can be characterized by an X-ray powder diffractogram comprising the following peaks: 6.4, 10.2, 13.6, and 17.0°2θ±0.2 °2θ. Compound I dihydrochloride Form 2 can be further characterized by an X-ray powder diffractogram comprising one or more peaks at: 20.4 or 25.1 °2θ±0.2 °2θ.

TG analysis (FIG. 6) of Compound I dihydrochloride Form 2 (which had been dried under vacuum at approximately 22° C. for about 15 h) showed weight loss of about 8.1% from the outset to 100° C., followed by weight loss of 1.1% between 200-250° C.

Similarly, a transient Compound I dihydrochloride Form 3 was recrystallized from methanol in solubility screen Experiment 10 as a wet solid. Form 3 can be characterized by the XRPD shown in FIG. 7. However, upon drying the isolated product under vacuum at about 30° C. for about 19-23 h, it was identified as Compound I dihydrochloride Form 2 by XRPD.

Compound I dihydrochloride Form 5

From solubility screening Experiment 24, a stirred solution of approximately 20 mg of amorphous Compound I dihydrochloride in approximately 100 µL of 2-propanol:water (95:5) at 50° C. was cooled at a rate of 0.1° C./min to 5° C. and was stirred for 10 h. Upon cooling, a thick slurry formed. The solids were isolated by centrifugation (0.22 µm nylon filter) and dried under vacuum at about 30° C. for about 19-23 h. The isolated crystalline solid was deemed to be Compound I dihydrochloride Form 5.

Compound I dihydrochloride Form 5 is crystalline by XRPD (FIG. 10) and can be characterized by an X-ray powder diffractogram comprising the following peaks: 5.8, 13.0, and 14.2 °2θ±0.2 °2θ. Compound I dihydrochloride Form 5 can be further characterized by an X-ray powder diffractogram comprising one or more peaks at: 16.3, 19.5, or 23.3 °2θ±0.2 °2θ.

TG analysis (FIG. 11) of Compound I dihydrochloride Form 5 (which had been dried under vacuum at approximately 22° C. for about 21 h) showed weight loss of about 5.1% from the outset to 75° C., followed by weight loss of 1.3% between 75-200° C., with further weight loss of 2.5% between 200-260° C.

Compound I dihydrochloride Form 5 was also recrystallized from acetone:water (50:50) after cooling and acetone anti-solvent addition in solubility screening Experiment 20 as a wet solid. Upon drying the wet isolate under vacuum at about 30° C. for about 19-23 h, the crystalline solid was identified as a mixture of Compound I dihydrochloride Forms 5 and 6 by XRPD.

Compound I dihydrochloride Form 4

From solubility screening Experiment 19, a stirred solution of approximately 20 mg of amorphous Compound I dihydrochloride in approximately 100 µL of water at 50° C. was cooled at a rate of 0.1° C./min to 5° C. and was stirred for 10 h. Upon cooling, a thick slurry formed. The wet solids were isolated by centrifugation (0.22 µm nylon filter) and were deemed to be Compound I dihydrochloride Form 4.

Compound I dihydrochloride Form 4 is crystalline by XRPD (FIG. 8) and can be characterized by an X-ray powder diffractogram comprising the following peaks: 3.6, 6.2, and 8.6 °2θ±0.2 °2θ. Compound I dihydrochloride Form 4 can be further characterized by an X-ray powder diffractogram comprising one or more peaks at: 24.0 or 25.6 02θ±0.2 °2θ.

TG analysis (FIG. 9) of Compound I dihydrochloride Form 4 which had been air-dried at approximately 22° C. for about 24 h showed weight loss of about 18.9% from the outset to 150° C., followed by weight loss of 0.6% between 150-250° C.

Upon drying the wet Compound I dihydrochloride Form 4 that recrystallized from water in solubility screening Experiment 19 under vacuum at about 30° C. for about 19-23 h, Compound I dihydrochloride Form 6 was provided.

Example 3. Thermodynamic Solubility Study

To obtain accurate solubility and residual solid form data for amorphous Compound I dihydrochloride, thermodynamic solubility studies were carried out on amorphous input material in selected solvent systems at 50° C. and 5° C. (Table 6).

The following procedure was used:
  Approximately 100 or 50 mg of amorphous Compound I dihydrochloride was weighed out into 24×1.5 mL screwcap vials.
  400 µL of the appropriate solvent system was added and the experiments were stirred at either 50° C. or 5° C.
  After 3 h, additional solvent aliquots (100 µL) were added if required to improve the mixing.
  Further solvent aliquots were added after 4, 5, 7, 7.5 and 21 h.
  Experiments were stirred at the required temperature for 23 h and then stirring halted and solids allowed to settle for about 2-3 h.

Mother liquors were filtered into pre-heated or pre-cooled vials (5 μm needle filter where possible; 0.45 μm syringe filter if slurry did not settle; centrifugation required for gels) for HPLC analysis.

The remaining slurries were separated by centrifugation (0.22 μm nylon filter) and isolated materials were analyzed by XRPD.

All isolated material was dried under vacuum at about 25° C. for about 17 h, then re-analyzed by XRPD.

TABLE 6

Thermodynamic Solubility Study

| Experiment | Solvent System (v/v) | Temperature/ ° C. | Input Mass/ mg | Input Volume/ μL | Additional Solvent Volume/ μL |
|---|---|---|---|---|---|
| 1 | Ethanol | 50 | 100.5 | 400 | — |
| 2 | Water | | 100.5 | 400 | — |
| 3 | 2-Propanol | | 100.0 | 400 | — |
| 4 | Acetone:Water 90:10 | | 100.6 | 400 | 300 |
| 5 | Acetone:Water 70:30 | | 100.6 | 400 | — |
| 6 | Acetone:Water 60:40 | | 100.7 | 400 | — |
| 7 | 2-Propanol:Water 99:1 | | 100.0 | 400 | 1000 |
| 8 | 2-Propanol:Water 95:5 | | 100.5 | 400 | 1000 |
| 9 | 2-Propanol:Heptane 90:10 | | 100.0 | 400 | 1000 |
| 10 | 2-Propanol:Heptane 70:30 | | 100.0 | 400 | 1000 |
| 11 | Ethanol:Heptane 80:20 | | 100.6 | 400 | — |
| 12 | Ethanol:Heptane 60:40 | | 100.0 | 400 | 1100 |
| 13 | Ethanol | 5 | 50.1 | 400 | 1100 |
| 14 | Water | | 50.3 | 400 | 200 |
| 15 | 2-Propanol | | 50.1 | 400 | 1100 |
| 16 | Acetone:Water 90:10 | | 50.0 | 400 | 900 |
| 17 | Acetone:Water 70:30 | | 50.5 | 400 | — |
| 18 | Acetone:Water 60:40 | | 50.3 | 400 | — |
| 19 | 2-Propanol:Water 99:1 | | 50.2 | 400 | 1100 |
| 20 | 2-Propanol:Water 95:5 | | 50.0 | 400 | 1000 |
| 21 | 2-Propanol:Heptane 90:10 | | 50.4 | 400 | 1100 |
| 22 | 2-Propanol:Heptane 70:30 | | 50.0 | 400 | 1100 |
| 23 | Ethanol:Heptane 80:20 | | 50.0 | 400 | 1100 |
| 24 | Ethanol:Heptane 60:40 | | 50.0 | 400 | 1100 |

Amorphous Compound I dihydrochloride had high solubility (>215 mg/mL) in ethanol, water, 2-propanol, acetone:water 70:30 and 60:40 v/v and ethanol:heptane 80:20 v/v at 50° C., with experiments remaining unsaturated. Moderate to high solubility (40-115 mg/mL) was obtained in acetone:water 90:10 v/v, 2-propanol:water 99:1 and 95:5 v/v, 2-propanol:heptane 90:10 v/v and ethanol:heptane 60:40 v/v at 50° C., suggesting that amorphous Compound I dihydrochloride remained soluble even in solvent mixtures containing a significant amount of antisolvent. Lower solubility (about 20 mg/mL) was obtained at 50° C. in 2-propanol:heptane 70:30 v/v.

At 5° C., amorphous Compound I dihydrochloride had high solubility (>125 mg/mL) in acetone:water 70:30 and 60:40 v/v, where experiments remained unsaturated, with high solubility (65 mg/mL) also obtained in water. The amorphous solid also had good to moderate solubility (10-40 mg/mL) at 5° C. in ethanol, 2-propanol, acetone:water 90:10 v/v, 2-propanol:water 99:1 and 95:5 v/v, 2-propanol:heptane 90:10 v/v and ethanol:heptane 80:20 v/v. Low solubility (<10 mg/mL) at 5° C. was only obtained in 2-propanol:heptane 70:30 v/v and ethanol:heptane 60:40 v/v, suggesting that a relatively high anti-solvent content would be required to obtain good yields from an anti-solvent addition crystallization.

Residual solids isolated from the thermodynamic solubility study Experiments 4, 7, and 8, carried out at 50° C. in water mixtures, were consistent by XRPD with Compound I dihydrochloride Form 5. Compound I dihydrochloride Form 4 was isolated from water at 5° C. (thermodynamic solubility study Experiment 14), which, when dried under vacuum at about 25° C. for about 17 h, provided poorly crystalline Compound I dihydrochloride Form 6. Compound I dihydrochloride Form 2 was isolated from ethanol:heptane 60:40 v/v at 50° C. (thermodynamic solubility study Experiment 12), and from ethanol and ethanol/heptane mixtures at 5° C. (thermodynamic solubility study Experiments 13 and 23/24, respectively), and was retained after drying under vacuum at about 25° C. for about 17 h.

TG analysis of the material isolated from 2-propanol:water 99:1 v/v at 50° C. and dried under vacuum at about 25° C. for about 17 h (thermodynamic solubility study Experiment 7, Compound I dihydrochloride Form 5) showed weight loss of about 9.9% from the outset to 60° C., followed by weight losses of 0.4% (between 60-210° C.) and 2.2% (between 210-260° C.).

TG analysis of the material isolated from ethanol:heptane 60:40 v/v at 50° C. and dried under vacuum at about 25° C. for about 17 h (thermodynamic solubility study Experiment 12, Compound I dihydrochloride Form 2) showed weight loss of about 7.4% from the outset to 100° C., followed by weight losses of 1.4% (between 100-200° C.) and 1.6% (between 200-250° C.).

TG analysis of the material isolated from ethanol:heptane 60:40 v/v at 5° C. and dried under vacuum at about 25° C. for about 17 h (thermodynamic solubility study Experiment 24, Compound I dihydrochloride Form 2) showed weight loss of about 6.5% from the outset to 100° C., followed by weight losses of 1.7% (between 100-200° C.) and 1.5% (between 200-250° C.).

Example 4. Small-Scale Crystallization

Initial Cooling/Anti-Solvent Addition Experiments

Small-scale crystallization Experiments 1 and 2, where initial cooling was followed by anti-solvent addition, were carried out.

About 300 mg of Compound I dihydrochloride Form 1 was dissolved in the solvent system with magnetic stirring. The mixtures were heated to 50° C. over about 15 min and stirred at 50° C. for 0.25 h. Additional solvent aliquots (100 μL) were added if required for dissolution. The solutions were polish filtered (0.2 μm PTFE filters) and then stirred at 50° C. for 0.25 h prior to cooling to 5° C. at 0.1° C./min.

Small-scale crystallization Experiment 2 had a further 1.5 mL of ethanol:heptane 80:20 v/v added, as a very thick slurry was obtained at 43° C.

After about 12 h at 5° C., anti-solvent addition was carried out at 5° C. over 0.5-1 h.

Small-scale crystallization Experiment 2 was sub-sampled prior to ASA, with solids isolated by centrifugation (0.22 μm nylon filter) and analyzed by XRPD.

Small-scale crystallization Experiment 1 formed gum during ASA and was not sub-sampled at this point.

After a further 3 h at 5° C., both experiments were sub-sampled and analyzed by XRPD. The experiments were stirred at 5° C. for a further 23 h and then sub-sampled again and analyzed by XRPD.

The solids were dried under vacuum at ambient temperature (about 23° C.) for 17 h. The solids on the XRPD plate were stored at 40° C./75% RH for 22 h then re-analyzed. Amorphous and a mixture of Compound I dihydrochloride Form 2 and Form 6 were obtained (Table 7).

TABLE 7

Summary of Results for Initial Cooling/Anti-Solvent Addition Experiments

| Expt # | Final Solvent System (v/v) | Observations | | | XRPD | |
|---|---|---|---|---|---|---|
| | | 12 h at 5° C. | ASA | 41.5 h at 5° C. | Dry | 40° C./ 75% RH |
| 1 | Acetone:Water (2:98) | Solution | Gum | Solid | Amorphous | Amorphous |
| 2 | Ethanol:Heptane (30:70) | Thick Slurry | Slurry | Slurry | Forms 2 & 6 | Forms 2 & 6 |

XRPD analysis of small-scale crystallization Experiment 1 showed that amorphous Compound I dihydrochloride was obtained after stirring for 3 h at 5° C. after the ASA was complete, after 23 h at 5° C. after the ASA was complete, on isolation, after drying under vacuum at about 23° C. for 17 h, and after storing the material at 40° C./75% RH.

TG analysis of the material isolated and dried under vacuum at about 23° C. for 17 h showed weight loss of about 9.1% from the outset to 200° C., followed by weight loss of 1.6% between 200-250° C.

XRPD analysis of small-scale crystallization Experiment 2 indicated that a mixture of Compound I dihydrochloride Form 2 and a form designated as Form 7 was obtained from the sub-sample after cooling and after ASA, with conversion to Form 2 observed after holding at 5° C. Predominantly Form 2 was isolated, with some Form 1 observed, which, when dried under vacuum at ambient temperature for 17 h, provided predominantly Compound I dihydrochloride Form 2, with some Form 6, and was maintained at 40° C./75% RH.

TG analysis of the material isolated and dried under vacuum at about 23° C. for 17 h showed weight loss of about 4.4% from the outset to 200° C., followed by weight loss of 1.0% between 200-250° C.

Initial Slurry Experiments

Small-scale crystallization Experiments 3 and 4 where performed, employing a mobile slurry form for the reaction medium.

Approximately 300 mg of Compound I dihydrochloride Form 1 was diluted to a mobile slurry in the appropriate solvent system, with magnetic stirring at 5° C. Additional solvent aliquots (1.0 mL) were added after 0.75 h and 6.5 h, if required to produce mobile slurries. The experiments were sub-sampled after 3 h and analyzed by XRPD.

Additional solid (100 mg) was added to small-scale crystallization Experiment 3, as the slurry dissolved during attempted isolation. After about 22 h at 5° C., the experiments were sub-sampled and analyzed by XRPD.

The solids were isolated by filtration after a total of 27.5 h at 5° C. and washed with 0.6 mL of cold acetone or 3×0.6 mL of cold heptane. The solids were dried under vacuum at ambient temperature (about 23° C.) for 17 h. The solids on the XRPD plate were stored at 40° C./75% RH for 22 h then re-analyzed by XRPD. Results, which are summarized in Table 8, show mixtures of Compound I dihydrochloride Forms 5 and 6, 5, 2 and 1, and 2 were obtained.

TABLE 8

Summary of Results for Initial Slurry Experiments

| Expt # | Final Solvent System (v/v) | Observations | | | XRPD | |
|---|---|---|---|---|---|---|
| | | 3 h | 22 h | 27.5 h | Dry | 40° C./ 75% RH |
| 3 | Acetone:Water (90:10) | Slurry | Slurry | Slurry | Forms 5 & 6 | Form 5 |
| 4 | Ethanol:Heptane (80:20) | Slurry | Slurry | Slurry | Forms 2 & trace 1 | Form 2 |

XRPD analysis for small-scale crystallization Experiment 3 sub-samples indicated that Compound I dihydrochloride Form 5 was obtained after 3 h at 5° C. and maintained throughout the experiment. A mixture of Form 5 and Form 6 was obtained after drying under vacuum at ambient temperature for 17 h, with conversion back to Compound I dihydrochloride Form 5 observed after storage at 40° C./75% RH. Conversion to Form 5 was also observed after storage at 5° C. for about 2 weeks.

TG analysis of the material isolated and dried under vacuum at ambient temperature for 17 h showed weight loss of about 4.5% from the outset to 60° C., followed by weight loss of 1.3% between 200-250° C.

XRPD analysis for small-scale crystallization Experiment 4 sub-samples indicated that Compound I dihydrochloride Form 3 was obtained after 3 h at 5° C., with Form 1 observed after 22 h. A mixture of Form 3 and Form 1 was obtained on isolation, which, when dried under vacuum at ambient temperature for 17 h, provided Form 2 with a trace Form 1. Compound I dihydrochloride Form 2 was obtained after storage at 40° C./75% RH.

TG analysis of the material isolated and dried under vacuum at ambient temperature for 17 h showed weight loss of about 6.7% from the outset to 200° C., followed by weight loss of 1.6% between 200-250° C.

Preparation of Compound I dihydrochloride Form 4 (Small-Scale Crystallization Experiment 5)

1.0 mL of water was added to approximately 300 mg of Compound I dihydrochloride Form 1. The resulting mixture was magnetically stirred at 50° C. over about 15 min, then stirred at 50° C. for 0.25 h. The solution was polish filtered (0.45 μm PTFE filter) into a 2 mL push-cap vial and then stirred at 50° C. for 0.25 h, prior to cooling to 5° C. at 0.1° C./min. After 62 h at 5° C., the experiment was sub-sampled and the solid was analyzed by XRPD. The material on the XRPD plate was dried under vacuum at 35° C. under a stream of wet nitrogen (20-38% RH) for about 9 h and then re-analyzed by XRPD. The material on the XRPD plate was stored at 25° C./60% RH for 22 h and then re-analyzed by XRPD. After a total of 87 h at 5° C., solids were isolated by centrifugation (0.22 μm nylon filter) and analyzed by XRPD. The solids were air-dried at ambient temperature (about 22° C.) for 24 h.

XRPD analysis (FIG. 8) indicated that Compound I dihydrochloride Form 4 was obtained after 62 h at 5° C. Drying the subsampled material under vacuum with wet nitrogen (RH=20-38%) resulted in conversion to Compound I dihydrochloride Form 6, which was maintained after storage at ambient conditions and at 25° C./60% RH. The bulk material, isolated after 87 h at 5° C., was consistent with Compound I dihydrochloride Form 4 and was retained after air-drying.

Compound I dihydrochloride Form 4 is crystalline by XRPD (FIG. 8) and can be characterized by an X-ray powder diffractogram comprising the following peaks: 3.6, 6.2, and 8.6 °2θ±0.2 °2θ. Compound I dihydrochloride Form 4 can be further characterized by an X-ray powder diffractogram comprising one or more peaks at: 24.0 or 25.6 °2θ±0.2 °2θ.

TG analysis (FIG. 9) of Compound I dihydrochloride Form 4 which had been air-dried at approximately 22° C. for about 24 h showed weight loss of about 18.9% from the outset to 150° C., followed by weight loss of 0.6% between 150-250° C.

Preparation of Compound I Dihydrochloride Form 5 (Small-Scale Crystallization Experiment 6)

Approximately 350 mg of Compound I dihydrochloride Form 1 was diluted with 2.0 mL of 2-propanol:water 99:1 v/v. The resulting mixture was magnetically stirred at 50° C. After 4 h at 50° C., further 200 μL aliquots of the solvent system were added to improve the mixing (a further 1.0 mL was added in total). After 20.5 h at 50° C., the experiment was sub-sampled and the solid was isolated by centrifugation (0.22 μm nylon filter) and analyzed by XRPD. The slurry was cooled from 50° C. to 20° C. at 0.5° C./min and stirred at 20° C. for 1 h. The solids were isolated by centrifugation (0.22 μm nylon filter) and analyzed by XRPD, then dried under vacuum at ambient temperature (about 22° C.) for 21 h.

XRPD analysis (FIG. 10) indicated that Compound I dihydrochloride Form 5 was obtained after 20.5 h at 50° C. and maintained after cooling, isolation and drying under vacuum at about 22° C. for 21 h.

Compound I dihydrochloride Form 5 is crystalline by XRPD (FIG. 10) and can be characterized by an X-ray powder diffractogram comprising the following peaks: 5.8, 13.0, and 14.2 °2θ±0.2 °2θ. Compound I dihydrochloride Form 5 can be further characterized by an X-ray powder diffractogram comprising one or more peaks at: 16.3, 19.5, or 23.3 °2θ±0.2 °2θ.

TG analysis (FIG. 11) of Compound I dihydrochloride Form 5 (which had been dried under vacuum at approximately 22° C. for about 21 h) showed weight loss of about 5.1% from the outset to 75° C., followed by weight loss of 1.3% between 75-200° C., with further weight loss of 2.5% between 200-260° C.

Cooling/Anti-Solvent Addition Experiments

Small-scale crystallization Experiments 7, 8, and 10, where investigating cooling followed by anti-solvent addition were performed.

Approximately 350 mg of Compound I dihydrochloride Form 1 was weighed into 3×20 mL screw-cap vials. Appropriate solvent systems were added, then the mixtures were magnetically stirred and heated to 50° C. over about 15 min and allowed to continue stirring at 50° C. for 0.25 h. Additional solvent aliquots (0.5 or 1.0 mL) were added if required for dissolution. The solutions were polish filtered (0.2 μm PTFE filters) and then cooled to 5° C. at 0.1° C./min.

Small-scale crystallization Experiment 7 had a further 3.5 mL of ethanol:water 99:1 v/v added in aliquots, as a very thick slurry was obtained during cooling.

After about 17 h at 5° C., anti-solvent addition was carried out at 5° C.

Small-scale crystallization Experiment 7 was sub-sampled prior to ASA and after ASA was complete, with solids isolated by centrifugation (0.22 μm nylon filter) and analyzed by XRPD.

Anti-solvent addition was carried out at 1 mL/h (about 3 volumes/h) for small-scale crystallization Experiments 7 and 8, and at 5 mL/h (about 14 volumes/h) for small-scale crystallization Experiment 10.

Where oiling was observed (small-scale crystallization Experiments 8 and 10), the mixtures were heated to 50° C. at 1° C./min and then re-cooled to 5° C. at 0.2° C./min.

The solids were isolated by filtration after about 1-2 h at 5° C. after ASA was complete and were washed with 2 volumes of the final solvent/anti-solvent mixture (at 5° C.). The solids were dried under vacuum at ambient temperature (about 22° C.) for about 15 h and analyzed by XRPD. Results, which are summarized in Table 9, show Compound I dihydrochloride Forms 2 and 5 were obtained.

TABLE 9

Summary of Results for Cooling/Anti-Solvent Addition Experiments

| Expt # | Final Solvent System (v/v) | Observation | | XRPD |
| --- | --- | --- | --- | --- |
| | | 5° C. | ASA | Dry |
| 7 | Ethanol:Water:Heptane (49.5:0.5:50) | Thick Slurry | Slurry | Form 2 |
| 8 | Acetone:Water:Heptane (72.5:2.5:25) | Solution | Oil [a] | Form 5 |
| 10 | Acetone:Water (97.5:2.5) | Solution | Oil [b] | Form 5 (Poorly Crystalline) |

[a] Recrystallized after 1 h at 50° C.
[b] Recrystallized after 1 h at 50° C. and re-cooling to 5° C.

Figure 5:
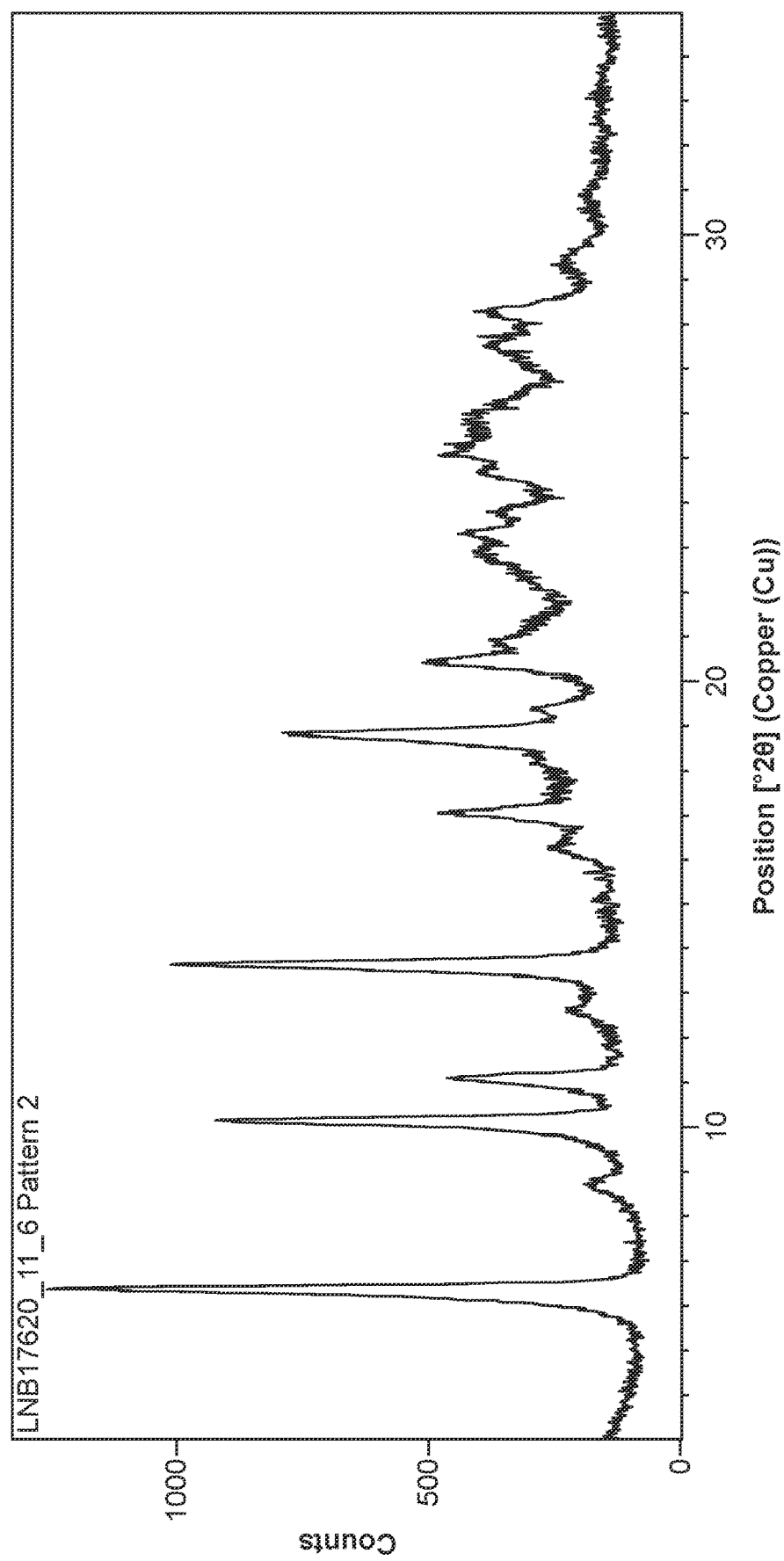
FIG. 5 is an X-ray powder diffractogram of Compound I dihydrochloride Form 2.

XRPD analysis for small-scale crystallization Experiment 7 sub-samples indicated that a new Compound I dihydrochloride Form 8 was initially observed after 16 h at 5° C. (see FIG. 14), which converted to Compound I dihydrochloride Form 2 after 1 h under ambient conditions, as observed by XRPD (FIG. 5). Compound I dihydrochloride Form 2 was isolated after ASA and after isolation and drying under vacuum at ambient temperature for about 15 h.

TG analysis (FIG. 6) of Compound I dihydrochloride Form 2 dried under vacuum at ambient temperature for about 15 h showed weight loss of about 8.1% from the outset to 100° C., followed by weight loss of 1.1% between 200-250° C.

Figure 10:
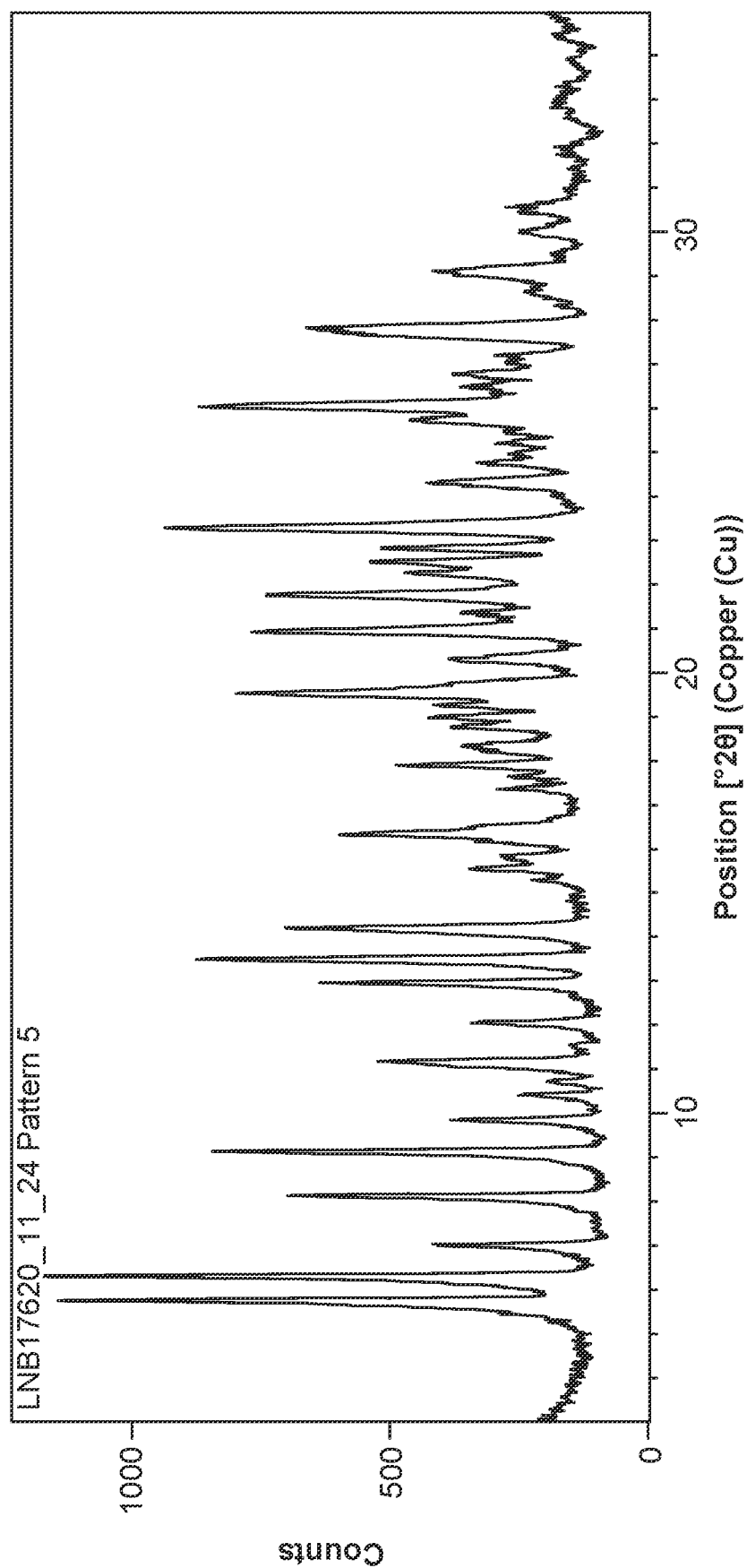
FIG. 10 is an X-ray powder diffractogram of Compound I dihydrochloride Form 5.

XRPD analysis for small-scale crystallization Experiment 8 sub-samples indicated that Compound I dihydrochloride Form 5 was isolated after ASA/cooling and after isolation and drying under vacuum at ambient temperature for about 15 h (FIG. 10). The dried material potentially contained a trace of Compound I dihydrochloride Form 1.

TG analysis (FIG. 11) of Compound I dihydrochloride Form 5 dried under vacuum at ambient temperature for about 15 h showed weight loss of about 2.8% from the outset to 75° C., followed by weight loss of 0.2% between 75-200° C., with further weight loss of 1.6% between 200-260° C.

XRPD analysis for small-scale crystallization Experiment 10 sub-samples indicated that poorly crystalline Compound I dihydrochloride Form 5 was obtained after ASA, re-cooling and stirring at 5° C., with no improvement in crystallinity after drying under vacuum at ambient temperature for about 15 h or isolation.

TG analysis of the material isolated and dried under vacuum at ambient temperature for about 15 h showed weight loss of about 9.7% from the outset to 200° C., with further weight loss of 1.7% between 200-260° C.

Anti-Solvent Addition/Cooling Experiment (Small-Scale Crystallization Experiment 9)

Anti-solvent addition was carried out prior to cooling to favor crystalline material and a mobile slurry. Approximately 350 mg of Compound I dihydrochloride Form 1 was diluted with 1.0 mL of 2-propanol:water 99:1 v/v. The mixture was magnetically stirred and heated to 50° C. over about 15 min, and allowed to further stir at 50° C. for 0.25 h. Further 1.0 mL aliquots of the solvent system were added, but thick slurry remained after addition of 3.0 mL and the experiment was continued using the slurry. Anti-solvent addition of 3 mL of heptane was carried out at 50° C. at 1 mL/h (about 3 volumes/h). The experiment was stirred at 50° C. for about 0.5 h after ASA was complete, then cooled to 5° C. at 0.1° C./min. After 12 h at 5° C., the experiment was sub-sampled and the solid was analyzed by XRPD. The material on the XRPD plate was re-analyzed after 1 h stored under ambient conditions. In an attempt to improve the crystallinity of the solids, the experiment was heated to 50° C. at 0.75° C./min and then re-cooled to 5° C. at 0.1° C./min. After a further 9 h at 5° C., the solids were isolated by filtration and washed with 2 volumes of 2-propanol:water: heptane 49.5:0.5:50 v/v/v (at 5° C.). The solids were dried under vacuum at ambient temperature (about 22° C.) for about 18 h.

XRPD analysis of the sub-samples indicated that poorly crystalline Compound I dihydrochloride Form 5 was obtained after ASA and cooling, with no improvement in crystallinity after drying under vacuum at ambient temperature for about 18 h, exposure to ambient conditions, repeating the heat/cool or isolation.

TG analysis of the material isolated and dried under vacuum at ambient temperature for about 18 h showed weight loss of about 5.4% from the outset to 200° C., followed by weight loss of 1.8% between 200-260° C.

Seeded Anti-Solvent Addition/Cooling Experiments

Small-scale crystallization Experiments 11, 12, and 13 where performed, employing variations of the ethanol/water/heptane solvent system, with seeded anti-solvent addition and cooling.

Approximately 350 mg of Compound I dihydrochloride Form 1 was diluted with the appropriate solvent system. The mixtures were then magnetically stirred and heated to 60° C. over about 15 min, then were allowed to stir at 60° C. for 0.25 h. The solutions were polish filtered (0.2 μm PTFE filters) and then cooled to 55° C. at 0.17° C./min. The experiments were seeded with about 3.5 mg (1 wt. %) of Compound I dihydrochloride Form 2 (obtained from small-scale crystallization Experiment 7 of Example 4). The seed did not persist, so the experiments were re-seed twice more. The experiments were cooled to 50° C. at 0.17° C./min and re-seeded (1 wt. % Form 2 from small-scale crystallization Experiment 7 of Example 4). Once again, the seed did not persist. Anti-solvent addition of heptane was carried out at 1 mL/h (about 3 volumes/h) for small-scale crystallization Experiment 11, and at 0.7 mL/h (about 2 volumes/h) for small-scale crystallization Experiments 12 and 13, until 10% of the total volume of anti-solvent had been added. The experiments were re-seeded with 1 wt. % of Compound I dihydrochloride Form 2 from small-scale crystallization Experiment 7 of Example 4, but the seed did not persist. Further aliquots of heptane (equivalent to 10% of the total volume of AS) were added, at the rates detailed above. The experiments were re-seeded with Compound I dihydrochloride Form 2 from small-scale crystallization Experiment 7 after each aliquot of anti-solvent had been added. Once seed persisted, the experiments were stirred at 50° C. for 1 h and then the remaining heptane was added at the appropriate rate. Once ASA was complete, the experiments were stirred at 50° C. for 0.25-3 h and then cooled from 50° C. to 5° C. at 0.1° C./min. After about 6 h at 5° C., solids were isolated by filtration and washed with 2 volumes of the appropriate solvent/anti-solvent mixture (ethanol:heptane 50:50 v/v or 40:60 v/v) at 5° C. The solids were dried under vacuum at ambient temperature (about 22° C.) for 18.5 h, then analyzed by XRPD. Results, which are summarized in Table 10, show a mixture of Compound I dihydrochloride Forms 7B and 2, and Compound I dihydrochloride Form 2 were obtained.

TABLE 10

Summary of Results for Seeded Anti-Solvent Addition/Cooling Experiments

| Expt # | Seed Crystal | Final Solvent System (v/v) | Observations | | XRPD Dry |
|---|---|---|---|---|---|
| | | | ASA | 5° C. | |
| 11 | Form 2 from Expt 7 | Ethanol:Heptane (50:50) | Slurry | Slurry | Forms 7B & 2 |
| 12 | Form 2 from Expt 7 | Ethanol:Water:Heptane (49.5:0.5:50) | Slurry | Slurry | Form 2 |
| 13 | Form 2 from Expt 7 | Ethanol:Water:Heptane (38:2:60) | Slurry | Thick Slurry* | Form 2 |

*Grainy slurry, material agglomerated

XRPD analysis of small-scale crystallization Experiment 11 indicated that Compound I dihydrochloride Form 7B was isolated, with partial conversion to Form 2 after drying under vacuum at about 22° C. for 18.5 h.

TG analysis of the material isolated and dried under vacuum at about 22° C. for 18.5 h showed weight loss of about 6.9% from the outset to 110° C., followed by weight loss of 1.8% between 110-250° C.

XRPD analysis of small-scale crystallization Experiment 12 indicated that Compound I dihydrochloride Form 2 was isolated and maintained after drying under vacuum at about 22° C. for 18.5 h.

TG analysis of the material isolated and dried under vacuum at about 22° C. for 18.5 h showed weight loss of about 8.3% from the outset to 110° C., followed by weight loss of 1.4% between 110-250° C.

XRPD analysis of small-scale crystallization Experiment 13 indicated poorly crystalline material predominantly consistent with Compound I dihydrochloride Form 2 was isolated and maintained after drying under vacuum at about 22° C. for 18.5 h.

TG analysis of the material isolated and dried under vacuum at about 22° C. for 18.5 h showed weight loss of about 8.1% from the outset to 125° C., followed by weight loss of 1.4% between 125-250° C.

Example 5. Thermodynamic Solubility Experiments at 60° C.

Approximately 250 mg of Compound I dihydrochloride Form 1 was dissolved in 0.5 mL of the appropriate solvent system, and the solutions were magnetically stirred at 60° C. Full dissolution was observed after 5-10 min at 60° C. in all experiments. After 3 h at 60° C., further solvent aliquots were added if required to obtain a mobile slurry. A further 100 mg of Compound I dihydrochloride Form 1 was added to the solutions. Further solvent aliquots were added if required after 4 h, 5.5 h, 6.5 h and 7.5 h. After 6.5 h at 60° C., the experiments, which remained solutions, were seeded with about 10 mg of Compound I dihydrochloride Form 2 (which can be prepared as described herein), which did not persist. After 23 h at 60° C., stirring was halted and the solids allowed to settle for about 2 h. The mother liquors were filtered (5 μm PTFE needle filter) into pre-heated vials for HPLC analysis. The solids were isolated by centrifugation (0.45 μm nylon filter) and analyzed by XRPD. The solids were dried under vacuum at ambient temperature (about 22° C.) for 67.5 h and then re-analyzed by XRPD. Results, which are summarized in Table 11, show Compound I dihydrochloride Form 7B was obtained.

XRPD analysis of the isolated solids for thermodynamic solubility Experiments 1 and 2 above indicated that a form designated as Compound I dihydrochloride Form 7 was isolated and maintained after drying under vacuum at about 22° C. for 67.5 h in both experiments. However, some peak shifting and small differences in the wet and dried diffractograms were noted, particularly for material isolated from ethanol:water 99:1 v/v (thermodynamic solubility Experiment 2). The diffraction pattern for the wet solid isolate has been designated Form 7A (see FIG. 13), and the diffraction pattern for the crystalline solid isolated and dried under vacuum at about 22° C. for 67.5 h has been designated Form 7B.

Example 6. Large-Scale Crystallization/Precipitation Trials

Large-Scale Crystallization Experiment 1

Approximately 5 g of Compound I dihydrochloride Form 1 was added to a 100 mL Easymax vessel. 25 mL of ethanol was added, and the experiment was stirred at 60° C. and 200 rpm (initial concentration: 200 mg/mL). Polish filtration was carried out (0.2 μm PTFE filter) and the solution was transferred into a clean 100 mL vessel. The solution was stirred at 60° C. and 200 rpm for about 0.25 h prior to cooling to 55° C. at 0.17° C./min. The solution was seeded with about 50 mg (1 wt. %) of Compound I dihydrochloride Form 2, isolated from small-scale crystallization Experiment 13, from example 4 above. The seed of Form 2 persisted. The resulting mixture was stirred at 55° C. for 1 h and then 25 mL of heptane was added at 1 vol/h. The experiment was stirred at 55° C. for 1 h after ASA was complete, then cooled to 5° C. at 0.1° C./min. The experiment was sub-sampled at 5° C. The slurry was very thick, and the mixing was poor. After 1.5 h at 5° C., the stirring rate was increased to 300 rpm and a further 30 mL of heptane was added at a rate of 3 vol/h (to obtain a solvent composition of ethanol:heptane 31:69 v/v). The stirring rate was increased to 400 rpm during heptane addition, as the slurry remained very thick. After a further 1 h at 5° C. after the second ASA was complete, a further 30 mL of ethanol was added in one portion, to obtain an ethanol:heptane ratio of 50:50 v/v. After a further 2 h at 5° C., solids were isolated by filtration and washed with 2 volumes of cold (5° C.) ethanol:heptane 50:50 v/v. The

TABLE 11

Summary of Results for Thermodynamic Solubility Experiments at 60° C.

| Expt # | Seed Crystal | Final Solvent System (v/v) | Observations | | | XRPD Dry |
|---|---|---|---|---|---|---|
| | | | Initial | 3 h | 22 h | |
| 1 | Form 2 | Ethanol | Dissolution | Thick, immobile slurry | Slurry | Form 7B |
| 2 | Form 2 | Ethanol:Water (99:1) | Dissolution | Solution | Slurry | Form 7B |
| 3 | Form 2 | Ethanol:Water (95:5) | Dissolution | Solution | Solution | No Solid | solids were filtered and dried under vacuum at ambient temperature (about 22° C.) for 15 h, then analyzed by XRPD.

XRPD analysis of large-scale crystallization Experiment 1 indicated that the sub-sampled material (isolated at 5° C., prior to the addition of further solvent and anti-solvent) was consistent with Compound I dihydrochloride Form 7A, which converted to Form 7B after drying under vacuum at about 22° C. for 15 h.

TG analysis of the material isolated and dried under vacuum at about 22° C. for 15 h showed weight loss of about 6.7% from the outset to 100° C., followed by weight loss of 2.3% between 100-250° C.

Large-Scale Crystallization Experiment 2

Approximately 5 g of Compound I dihydrochloride Form 1 was added to a 100 mL Easymax vessel. 15 mL of ethanol:water 99:1 v/v was added, and the experiment was stirred at 60° C. and 200 rpm (initial concentration: 333 mg/mL). Polish filtration was carried out (0.2 μm PTFE filter) and the solution was transferred into a clean 100 mL vessel. The solution was stirred at 60° C. and 200 rpm for about 0.25 h prior to cooling to 55° C. at 0.17° C./min. The solution was seeded with about 50 mg (1 wt. %) of Compound I dihydrochloride Form 2, isolated from small-scale crystallization Experiment 13, from example 4 above. The seed dissolved within 0.5 h. Anti-solvent addition of 2.5 mL (0.5 volumes) of heptane was carried out at 1 vol/h. The solution was re-seeded with a further 50 mg (1 wt. %) of Form 2, isolated from small-scale crystallization Experiment 13 of Example 4. The seed persisted and a slurry formed. The experiment was stirred at 55° C. for 1 h and then 20 mL of heptane was added at 1 vol/h. The experiment was cooled to 5° C. at 0.1° C./min. The experiment was sub-sampled at 5° C. The slurry was very thick, and the mixing was poor. After 2 h at 5° C., the stirring rate increased to 300 rpm and a further 30 mL of heptane was added at a rate of 3 vol/h (to obtain a solvent composition of ethanol:water:heptane 22:0.2:77.8 v/v/v). The stirring rate was increased to 400 rpm during heptane addition, as the slurry remained very thick. After a further 1 h at 5° C. after the second ASA was complete, a further 20 mL of ethanol:water 99:1 v/v was added in one portion, to obtain an ethanol:water:heptane ratio of 39.6:0.4:60 v/v/v. After a further 2 h at 5° C., solids were isolated by filtration and washed with 2 volumes of cold (5° C.) ethanol:heptane 40:60 v/v. The solids were filtered and dried under vacuum at ambient temperature (about 22° C.) for 15 h, then analyzed by XRPD.

XRPD analysis of large-scale crystallization Experiment 2 indicated that the sub-sampled material (isolated at 5° C., prior to the addition of further solvent and anti-solvent) was consistent with a mixture of Compound I dihydrochloride Form 7A and Form 2, which converted to a mixture of Form 7B and Form 2 after drying under vacuum at about 22° C. for 15 h. The isolated material was consistent with a mixture of Form 2 and either Form 1 or Form 3, and, when dried under vacuum at about 22° C. for 15 h, converted to Form 2.

TG analysis of the material dried under vacuum at about 22° C. for 15 h showed weight loss of about 5.5% from the outset to 100° C., followed by weight loss of 2.1% between 100-260° C.

Large-Scale Crystallization Experiment 3

Approximately 10 g of Compound I dihydrochloride Form 1 was dissolved in 67 mL of ethanol:water 99:1 v/v at about 60° C. (initial concentration: 150 mg/mL). Polish filtration was carried out (0.2 μm PTFE filter). The solution was transferred to a 250 mL vessel at 60° C. and stirred at 50° C. (solution temperature) and 300 rpm for about 5 min. The solution was seeded with about 100 mg (1 wt. %) of Compound I dihydrochloride Form 2, isolated from small-scale crystallization Experiments 12 and 13, from example 4 above. The seed dissolved rapidly. Anti-solvent addition of 10 mL of heptane (1 volume) was carried out at 2 vol/h (Heptane content of 13%). The solution was re-seeded with a further 100 mg (1 wt. %) of Form 2, isolated from small-scale crystallization Experiment 12. The seed persisted and a slurry formed. The slurry was stirred at 50° C. for 1 h and then anti-solvent addition of 131 mL of heptane at 1.5 vol/h was carried out, to reach 60% heptane. A thick slurry was noted at the beginning of ASA, so the stirring rate was increased to 350 rpm. An additional 2 volumes of ethanol:water 99:1 v/v was added at the beginning of the ASA to mobilize the slurry. Once ASA was complete, the slurry was cooled to 5° C. at 0.1° C./min. The experiment was sub-sampled after about 2 h at 5° C. The slurry was thick but mixing. After 3.5 h at 5° C., an additional 3.6 mL of water was added to increase the water content to 2% (ethanol:water:heptane ratio of 39:2:59 v/v/v). The experiment was sub-sampled again after 2 h at 5° C. with additional water. After a total of 10 h at 5° C., solids were isolated by filtration and washed with 2 volumes of cold (5° C.) ethanol:heptane 40:60 v/v. The solids were filtered and dried under vacuum at ambient temperature (about 21° C.) for 14.5 h, then analyzed by XRPD.

XRPD analysis of large-scale crystallization Experiment 3 indicated that the sub-sampled material (isolated after 2 h at 5° C.) was consistent with a mixture of Compound I dihydrochloride Form 7A and Form 7B. After the addition of water, the sub-sampled material had a diffractogram consistent with Compound I dihydrochloride Form 8 (similar to Form 2), which converted to Form 2 after 3 h under ambient conditions. The wet isolated material was consistent with Form 8. When dried under vacuum at about 21° C. for 14.5 h, the material was identified as predominantly Compound I dihydrochloride Form 2.

TG analysis of the material dried under vacuum at about 21° C. for 14.5 h showed weight loss of about 4.0% from the outset to 110° C., followed by weight loss of 1.8% between 110-260° C.

Large-Scale Crystallization Experiment 4

Approximately 10 g of Compound I dihydrochloride Form 1 was dissolved in 87 mL of ethanol:water 99:1 v/v at about 60° C. (initial concentration: 115 mg/mL). Polish filtration was carried out (0.2 μm PTFE filter). The solution was transferred to a 250 mL vessel at 60° C. and stirred at 250 rpm. The solution was cooled to 50° C. over 0.5 h (about 0.3° C./min) and stirring was maintained at 250 rpm. Anti-solvent addition of 10 mL of heptane (1 volume) was carried out in one portion (heptane content of 10%). The solution was seeded with about 100 mg (1 wt. %) of Compound I dihydrochloride Form 2, isolated from large-scale crystallization Experiment 2 from example 6. The seed persisted and a slurry formed. The slurry was stirred at 50° C. for 2 h and then anti-solvent addition of 120 mL of heptane at 2 vol/h was carried out, to reach 60% heptane. The slurry was thick but remained stirrable throughout. The experiment was sub-sampled 2 h after seeding, and at 36, 48 and 58% v/v heptane. Once ASA was complete, the slurry was stirred at 50° C. for about 0.5 h and then cooled to 25° C. at 0.1° C./min. After 15 h at 25° C., the solids were isolated by filtration and washed with 2 volumes of cold (5° C.) ethanol: heptane 40:60 v/v. The solids were dried under vacuum at ambient temperature (about 20° C.) for 17.5 h, then analyzed by XRPD. A sub-sample of the dried solid was dried under vacuum at 40° C. for about 18 hours.

XRPD analysis of large-scale crystallization Experiment 4 indicated that Compound I dihydrochloride Form 7 was obtained throughout the experiment, despite seeding with Form 2. Predominantly, crystalline Form 7A was obtained for the sub-samples, with a mixture of Form 7A and Form 7B obtained at 48% heptane, likely due to drying during centrifuge filtration. After isolation, the material was predominantly consistent with Compound I dihydrochloride Form 7B (some Form 7A present in wet samples), likely due to drying on the filter, with Form 7B obtained after drying under vacuum at about 20° C. for 17.5 h. Some loss in crystallinity was noted in the sub-sample of material which was dried at 40° C.

TG analysis of the material dried under vacuum at about 20° C. for 17.5 h showed weight loss of about 5.5% from the outset to about 75° C.

DVS analysis of the material dried under vacuum at about 20° C. for 17.5 h indicated that there was uptake of 8.7% between 20-70% RH (cycle 2 sorption). This may be attributed to deliquescence and form change at high humidity, as uptake of about 3% was observed between 40-80% RH during cycle 1 sorption, with a large uptake observed between 80-90% RH. Post-DVS XRPD analysis suggested that Compound I dihydrochloride Form 7B deliquesced at about 90% RH, as amorphous material was recovered.

Large-Scale Crystallization Experiment 5

Approximately 10 g of Compound I dihydrochloride Form 2 and Form 7B (from large-scale crystallization Experiments 1-3) was dissolved in 87 mL of ethanol:water 99:1 v/v at about 60° C. (initial concentration: 115 mg/mL). The solution was transferred to a 250 mL vessel at 60° C. and stirred at 250 rpm. The solution was cooled to 50° C. over 0.5 h (about 0.3° C./min) and stirring was maintained at 250 rpm. Anti-solvent addition of 5 mL of heptane (0.5 volumes) was carried out in one portion (heptane content of 5%). The solution was seeded with about 100 mg (1 wt. %) of Compound I dihydrochloride Form 7B, isolated from large-scale crystallization Experiment 1 from example 6. The seed persisted and a slurry formed. The slurry was stirred at 50° C. for 3 h and then anti-solvent addition of 125 mL of heptane at 1 vol/h was carried out, to reach 60% heptane. The slurry was thick but remained stirrable throughout. The experiment was sub-sampled 3 h after seeding. Once ASA was complete, the slurry was stirred at 50° C. for about 1.5 h and then cooled to 5° C. at 0.1° C./min. After 4 h at 5° C., solids were isolated by filtration and washed with 2 volumes of cold (5° C.) ethanol:heptane 40:60 v/v. The solids were dried under vacuum at ambient temperature (about 20° C.) for 18.5 h, then analyzed by XRPD. A sub-sample of the dried solid was dried under vacuum at 40° C. for about 18 hours.

XRPD analysis of large-scale crystallization Experiment 5 indicated that the sub-sampled material was consistent with Compound I dihydrochloride Form 7A, while the solids that were dried under vacuum at about 20° C. for 18.5 h were consistent with Form 7B. Minor peak shifting was noted after drying at 40° C., but no significant loss of crystallinity was observed.

Compound I dihydrochloride Form 7B is crystalline by XRPD (FIG. 1) and can be characterized by an X-ray powder diffractogram comprising the following peaks: 4.5, 9.1, 11.9, and 14.4°2θ±0.2 °2θ. Compound I dihydrochloride Form 7B can be further characterized by an X-ray powder diffractogram comprising one or more peaks at: 18.1, 20.0, or 22.3 °2θ±0.2 °2θ.

TG analysis (FIG. 2) of Compound I dihydrochloride Form 7B, which was dried under vacuum at about 20° C. for 18.5 h, showed weight loss of about 5.0% from the outset to about 75° C.

Large-Scale Crystallization Experiment 6

Approximately 10 g of Compound I dihydrochloride Form 7B was added to a 250 mL vessel and dissolved in 87 mL of ethanol:water 99:1 v/v at 60° C. (initial concentration: 115 mg/mL) with stirring at 250 rpm. The solution was cooled to 50° C. over 0.5 h (about 0.3° C./min) and stirring maintained at 250 rpm. Anti-solvent addition of 5 mL of heptane (0.5 volumes) was carried out in one portion (heptane content of 5%). The solution was seeded with about 100 mg (1 wt. %) of Compound I dihydrochloride Form 7B, isolated from large-scale crystallization Experiment 5 from example 6. The seed persisted and a slurry formed. The slurry was stirred at 50° C. for 2.3 h and then anti-solvent addition of 125 mL of heptane at 4 vol/h was carried out, to reach 60% heptane. The slurry was thick but remained stirrable throughout. Once ASA was complete, the slurry was stirred at 50° C. for about 1 h and then cooled to 5° C. at 0.1° C./min. After 7 h at 5° C., solids were isolated by filtration and washed with 2 volumes of cold (5° C.) ethanol:heptane 40:60 v/v. The solids were dried under vacuum at about 40° C. for 22.5 h, then analyzed by XRPD.

XRPD analysis of large-scale crystallization Experiment 6 indicated that the isolated wet solids were consistent with a mixture of Compound I dihydrochloride Form 7A and Form 7B, likely due to drying of material on the filter. Upon drying under vacuum at about 40° C. for 22.5 h, the resulting solids were consistent with Form 7B, with slight peak shifting observed and attributed to drying at 40° C.

TG analysis of the material dried under vacuum at about 40° C. for 22.5 h showed weight loss of about 6.7% from the outset to about 75° C.

Example 7. Thermodynamic Aqueous Solubility Experiments

To assess the aqueous solubility of the crystalline materials isolated from large-scale crystallization Experiments 1-6, thermodynamic aqueous solubility Experiments 1-6 were carried out at 25° C. and 5° C.

Approximately 100-200 mg of crystalline solid from large-scale crystallization Experiments 1-6 was dissolved with 500 or 1000 μL of water and the slurries were magnetically stirred at the required temperature. After 0.75, 2.5 and 6 h, additional 100 μL aliquots of water were added until mobile slurries were obtained. After 22 h, stirring was halted and the solids allowed to settle for about 2 h. The mother liquors were filtered (5 μm PTFE needle filter) into preheated or pre-cooled vials for HPLC analysis. The solids were isolated by centrifugation (0.45 μm nylon filter) and analyzed by XRPD. For the large-scale crystallization Experiments 1-3 input material at 25° C., solids on the XRPD plate were dried under vacuum at ambient temperature (about 21° C.) for about 22 h and then re-analyzed by XRPD. Results, which are summarized in Table 12, show Compound I dihydrochloride Forms 4 and 6 were obtained.

TABLE 12

Summary of Results for Thermodynamic Aqueous Solubility Experiments

| | | Observations | | XRPD | | |
| | Input | | | 25° C. | | 5° C. |
| Experiment | Material | 25° C. | 5° C. | Wet | Dry | Wet |
|---|---|---|---|---|---|---|
| 1 | 7B | Mobile Slurry | Mobile Slurry | Form 4 | Form 6 (Poorly Crystalline) | Form 4 |
| 2 | 2 | Mobile Slurry | Mobile Slurry | Form 4 | Form 6 (Poorly Crystalline) | Form 4 |
| 3 | 2 | Mobile Slurry | Mobile Slurry | Form 4 | Form 6 (Poorly Crystalline) | Form 4 |
| 4 | 7B | Mobile Slurry | Mobile Slurry | Form 4 | — | Form 4 |
| 5 | 7B | Thin Slurry | Thin Slurry | No Solid | — | No Solid |
| 6 | 7B | Thin Slurry | Thin Slurry | No Solid | — | No Solid |

Where solids were isolated, XRPD analysis showed that the wet diffractograms were consistent with Compound I dihydrochloride Form 4. If the material was dried under vacuum at ambient temperature for about 22 h, poorly crystalline Compound I dihydrochloride Form 6 was obtained.

Compound I dihydrochloride Form 6 is crystalline by XRPD (FIG. 12) and can be characterized by an X-ray powder diffractogram comprising the following peaks: 8.7, 15.7, and 24.8 °2θ±0.2 °2θ. Compound I dihydrochloride Form 6 can be further characterized by an X-ray powder diffractogram comprising one or more peaks at: 6.6 or 12.0 °2θ±0.2 °2θ.

Example 8. Salt Break and Salt Formation Experiments

Approximately 500 mg of Compound I dihydrochloride Form 1 was diluted in 40 mL of dichloromethane (DCM) and stirred at ambient temperature (about 21° C.). Approximately 40 mL of saturated potassium carbonate was added and the biphasic solution was stirred at ambient temperature (about 21° C.) for 1 h. Full dissolution was observed on addition of the base. The biphasic solution was separated. The organic layer was washed with 40 mL of water and the aqueous layer was washed with 2×40 mL of DCM. The combined organic layers were dried over sodium sulfate for about 1 h. The DCM was removed under reduced pressure. The oil obtained was re-dissolved in about 5 mL of DCM and the solvent was removed under reduced pressure to yield crispy solid. The solid was dried under vacuum at ambient temperature (about 21° C.) for 18 h. XRPD analysis of the isolated material indicated that it was amorphous solid.

Approximately 200 mg of amorphous Compound I free base was dissolved in 3.26 mL (16 volumes) of ethyl acetate and stirred at ambient temperature (about 21° C.) for about 0.25 h. 4 eq. of HCl were then added dropwise (1 M HCl in ethyl acetate used). Upon acidification, immediate precipitation was noted. The slurry was stirred at ambient temperature (about 21° C.) for about 2.5 h. The solid was isolated by filtration and washed with ethyl acetate (1 mL×2). The solid was dried under vacuum at ambient temperature (about 21° C.) for about 17 h. The prepared HCl salt of Compound I was characterized by XRPD, TG/DTA, and DVS. XRPD analysis indicated that the isolated material was amorphous.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

What is claimed is:

1. A crystalline form of Compound I dihydrochloride having the formula:

Compound I dihydrochloride

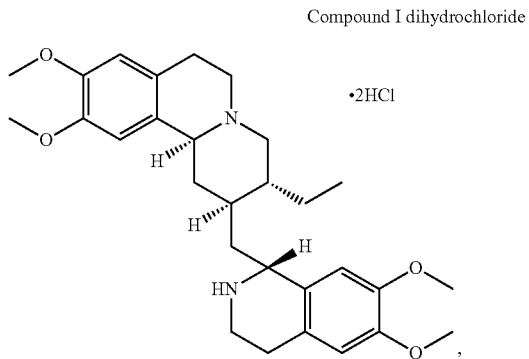

·2HCl selected from: Compound I dihydrochloride Form 7B, Compound I dihydrochloride Form 2, Compound I dihydrochloride Form 3, Compound I dihydrochloride Form 4, Compound I dihydrochloride Form 5, Compound I dihydrochloride Form 6, Compound I dihydrochloride Form 7A, and Compound I dihydrochloride Form 8.

2. A crystalline form of Compound I dihydrochloride having the formula:

Compound I dihydrochloride

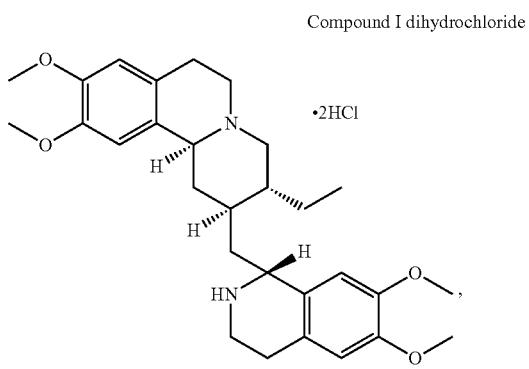

·2HCl characterized by an X-ray powder diffractogram comprising the following peaks: 4.5, 9.1, 11.9, and 14.4 °2θ+0.2 °2θ, as determined on a diffractometer using Cu-Kα radiation.

3. The crystalline form of claim 2, wherein the diffractogram further comprises one or more peaks at: 18.1, 20.0, or 22.3 °2θ+0.2°2θ.

4. The crystalline form of claim 2, wherein the crystalline form is characterized by the X-ray powder diffractogram as substantially shown in FIG. 1.

5. The crystalline form of claim 1, wherein the crystalline form is Compound I dihydrochloride Form 2 characterized by an X-ray powder diffractogram comprising the following peaks: 6.4, 10.2, 13.6, and 17.0 °2θ+0.2 °2θ, as determined on a diffractometer using Cu-Kα radiation.

6. The crystalline form of claim 1, wherein the crystalline form is Compound I dihydrochloride Form 4 characterized by an X-ray powder diffractogram comprising the following peaks: 3.6, 6.2, and 8.6 °2θ+0.2 °2θ, as determined on a diffractometer using Cu-Kα radiation.

7. The crystalline form of claim 1, wherein the crystalline form is Compound I dihydrochloride Form 5 characterized by an X-ray powder diffractogram comprising the following peaks: 5.8, 13.0, and 14.2 °2θ+0.2 °2θ, as determined on a diffractometer using Cu-Kα radiation.

8. The crystalline form of claim 1, wherein the crystalline form Compound I dihydrochloride Form 6 is characterized by an X-ray powder diffractogram comprising the following peaks: 8.7, 15.7, and 24.8 °2θ+0.2 °2θ, as determined on a diffractometer using Cu-Kα radiation.

9. A pharmaceutical composition comprising a crystalline form of claim 1 and a pharmaceutically acceptable carrier.

10. The pharmaceutical composition of claim 9, wherein at least 99% of Compound I dihydrochloride is in a crystalline form characterized by an X-ray powder diffractogram comprising the following peaks: 4.5, 9.1, 11.9, and 14.4 °2θ+0.2 °2θ, as determined on a diffractometer using Cu-Kα radiation.

11. A pharmaceutical composition of claim 9, further comprising one or more additional therapeutic agents.

12. The pharmaceutical composition of claim 11, wherein the one or more additional therapeutic agents is an antiparasitic agent.

13. The pharmaceutical composition of claim 12, wherein the antiparasitic agent is chloroquine or hydroxychloroquine.

14. The pharmaceutical composition of claim 11, wherein the one or more additional therapeutic agents is an antibiotic.

15. The pharmaceutical composition of claim 14, wherein the antibiotic is azithromycin.

16. The pharmaceutical composition of claim 11, wherein the one or more additional therapeutic agents is an antiviral agent.

17. The pharmaceutical composition of claim 16, wherein the antiviral agent is interferon, ribavirin, adefovir, tenofovir, acyclovir, brivudin, cidofovir, fomivirsen, foscarnet, ganciclovir, penciclovir, amantadine, rimantadine, lopinavir, ritonavir, zanamivir, or a combination thereof.

18. The pharmaceutical composition of claim 16, wherein the antiviral agent is remdesivir.

19. The pharmaceutical composition of claim 11, wherein the one or more additional therapeutic agents is an agent useful for controlling a cytokine storm.

20. The pharmaceutical composition of claim 19, wherein the agent useful for controlling a cytokine storm is ozanimod or fingolimod.

21. A method of treating a viral infection in a subject in need thereof, the method comprising administering to the subject a therapeutically effective amount of a crystalline form of claim 1, wherein the viral infection is a Flavivirus infection.

22. The method of claim 21, wherein the Flavivirus infection is Zika virus, West Nile virus, dengue virus, tick-borne encephalitis virus, Japanese encephalitis virus, St. Louis encephalitis virus, or yellow fever virus.

23. A method of treating a viral infection in a subject in need thereof, the method comprising administering to the subject a therapeutically effective amount of a crystalline form of claim 1, wherein the viral infection is caused by Zika virus (ZIKV), Ebola virus (EBOV), Rabies lyssavirus (RABV), cytomegalovirus (CMV), human immunodeficiency virus 1 (HIV-1), influenza A virus, Rift Valley fever virus (RVFV), echovirus 1 (EV1), human metapneumorivus (HMPV), or herpes simplex virus type 2 (HSV-2).

24. A method of treating a viral infection in a subject in need thereof, the method comprising administering to the subject a therapeutically effective amount of a crystalline form of claim 1, wherein the viral infection is caused by a coronavirus, wherein the coronavirus is 229E, NL63, OC43, HKU1, MERS-COV, SARS-COV, or SARS-COV-2.

25. A method of treating a viral infection in a subject in need thereof, the method comprising administering to the subject a therapeutically effective amount of a crystalline form of claim 1, wherein the viral infection is caused by severe acute respiratory syndrome coronavirus 2 (SARS-COV-2), and wherein the subject does not require hospitalization.

26. A method of treating a disease caused by severe acute respiratory syndrome coronovirus 2 (SARS-COV-2), in a subject in need thereof, comprising administering a therapeutically effective amount of a crystalline form of claim 1, and wherein the disease is COVID-19 and the subject does not require hospitalization.

27. The method of claim 25, wherein the subject does not exhibit severe symptoms of Cytokine Release Syndrome (cytokine storm).

* * * * *